United States Patent
El Qacemi et al.

(10) Patent No.: US 9,661,850 B2
(45) Date of Patent: *May 30, 2017

(54) METHODS OF SOIL PEST CONTROL

(71) Applicant: Syngenta Participations AG, Basel (CH)

(72) Inventors: Myriem El Qacemi, Stein (CH); Jerome Yves Cassayre, Stein (CH); Benedikt Kurtz, Stein (CH)

(73) Assignee: Syngenta Participations AG, Basel (CH)

( * ) Notice: Subject to any disclaimer, the term of this patent is extended or adjusted under 35 U.S.C. 154(b) by 11 days.

This patent is subject to a terminal disclaimer.

(21) Appl. No.: 14/423,177

(22) PCT Filed: Aug. 9, 2013

(86) PCT No.: PCT/EP2013/066691
§ 371 (c)(1),
(2) Date: Feb. 23, 2015

(87) PCT Pub. No.: WO2014/029639
PCT Pub. Date: Feb. 27, 2014

(65) Prior Publication Data
US 2015/0208655 A1    Jul. 30, 2015

(30) Foreign Application Priority Data

Aug. 24, 2012 (EP) .................... 12181767
Nov. 30, 2012 (EP) .................... 12195023

(51) Int. Cl.
*A01N 43/80* (2006.01)
*G06Q 30/00* (2012.01)

(52) U.S. Cl.
CPC ........... *A01N 43/80* (2013.01); *G06Q 30/018* (2013.01)

(58) Field of Classification Search
None
See application file for complete search history.

(56) References Cited

U.S. PATENT DOCUMENTS 8,735,362 B2 * 5/2014 Cassayre .............. C07D 413/12
514/202
9,320,278 B2 * 4/2016 El Qacemi ............. A01N 43/80

FOREIGN PATENT DOCUMENTS

| WO | 2011067272 | 6/2011 |
|---|---|---|
| WO | 2012067235 | 5/2012 |
| WO | 2013050302 | 4/2013 |

OTHER PUBLICATIONS

International Search Report Dated Dec. 16, 2013 for International Patent Application No. PCT/EP2013/066691.

* cited by examiner

*Primary Examiner* — Kamal Saeed
(74) *Attorney, Agent, or Firm* — R. Kody Jones

(57) ABSTRACT

The present invention relates to methods of controlling and/or preventing soil-dwelling pests in useful plants comprising applying to the locus of the useful plant or treating plant propagation material thereof with a compound of formula (I) wherein —$B^1$—$B^2$—$B^3$— is —C=N—O—, —C=N—$CH_2$—, —C=$CH_2$—O— or —N—$CH_2$—$CH_2$—; L is a direct bond or methylene; $A^1$ and $A^2$ are C—H, or one of $A^1$ and $A^2$ is C—H and the other is N; $X^1$ is group X, formula (X) $R^1$ is $C_1$-$C_4$alkyl, $C_1$-$C_4$aloalkyl or $C_3$-$C_6$cycloalkyl; $R^2$ is chlorodifluoromethyl or trifluoromethyl; each $R^3$ is independently bromo, chloro, fluoro or trifluoromethyl; $R^4$ is hydrogen, halogen, methyl, halomethyl or cyano; $R^5$ is hydrogen; or $R^4$ and $R^5$ together form a bridging 1,3-butadiene group; p is 2 or 3. Preferably the soil-dwelling pest is selected from corn rootworm, wireworms, grubs, in particular white grubs (e.g. *Phyllophaga* sp., *Diloboderus* sp., *Popillia japonica*), termites (in particular for sugar cane), subterraneous stinkbugs (e.g. *Scaptocoris* sp.), cutworms (e.g. *agrotis* sp.), millipedes (e.g. *Julus* sp.) and broca gigante (e.g. *Telchin licus*).

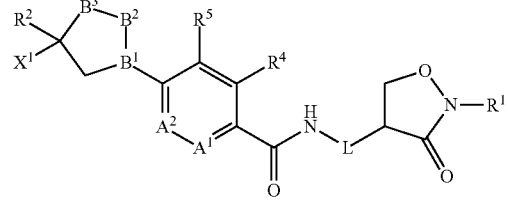

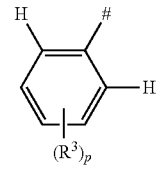

14 Claims, No Drawings

METHODS OF SOIL PEST CONTROL

RELATED APPLICATION INFORMATION

This application is a 371 of International Application No. PCT/EP2013/066691, filed 9 Aug. 2013, which claims priority to EP Patent Application No. 12181767.0, filed 24 Aug. 2012; EP Patent Application No. 12195023.2 filed 30 Nov. 2012, the contents of which are incorporated herein by reference herein.

The present invention relates to methods of soil pest control and in particular to control of corn rootworm, wireworms, grubs, in particular white grubs, termites, subterraneous stinkbugs, cutworms, millipedes and broca gigante.

Compounds that are insecticidally, acaricidally, nematicidally and/or moluscicidally active by antagonism of the gamma-aminobutyric acid (GABA)-gated chloride channel, and which comprise a partially saturated heterocycle that is substituted by a haloalkyl substituent and one or two optionally substituted aromatic or heteroaromatic rings, represent a new class of pesticides that are described for example in Ozoe et al. Biochemical and Biophysical Research Communications, 391 (2010) 744-749. Compounds from this class are broadly described in WO 2005/085216 (EP 1731512), WO 2007/123853, WO 2007/075459, WO2009/002809, WO 2008/019760, WO 2008/122375, WO 2008/128711, WO 2009/097992, WO 2010/072781, WO 2010/072781, WO 2008/126665, WO 2007/125984, WO 2008/130651, JP 2008110971, JP 2008133273, JP 2009108046, WO 2009/022746, WO 2009/022746, WO 2010/032437, WO 2009/080250, WO 2010/020521, WO 2010/025998, WO 2010/020522, WO 2010/084067, WO 2010/086225, WO 2010/149506 and WO 2010/108733.

It has now surprisingly been found that particular insecticides from this new class of gamma-aminobutyric acid (GABA)-gated chloride channel antagonists (disclosed in e.g. WO 2011/067272) are highly effective at controlling soil pests, in particular corn rootworm, wireworms, grubs, in particular white grubs, termites, subterraneous stinkbugs, cutworms, millipedes and broca gigante. These compounds represent an important new solution for soil pests, particularly corn rootworm, wireworms, grubs, in particular white grubs, termites, subterraneous stinkbugs, cutworms, millipedes and broca gigante, and particularly where the soil pests are resistant to current methods.

In a first aspect the invention provides a method of controlling and/or preventing soil-dwelling pests in useful plants comprising applying to the locus of the useful plant or treating propagation material thereof, preferably a seed, with a compound of formula I

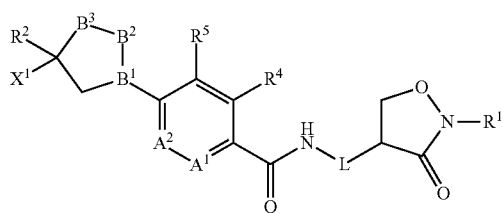

(I)

wherein
—B$^1$—B$^2$—B$^3$— is —C=N—O—, —C=N—CH$_2$—, —C=CH$_2$—O— or —N—CH$_2$—CH$_2$—;
L is a direct bond or methylene;
A$^1$ and A$^2$ are C—H, or one of A$^1$ and A$^2$ is C—H and the other is N;
X$^1$ is group X

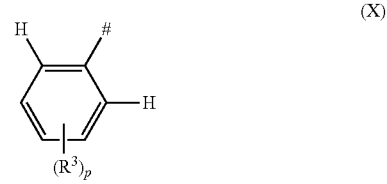

(X)

R$^1$ is C$_1$-C$_4$alkyl, C$_1$-C$_4$haloalkyl or C$_3$-C$_6$cycloalkyl;
R$^2$ is chlorodifluoromethyl or trifluoromethyl;
each R$^3$ is independently bromo, chloro, fluoro or trifluoromethyl;
R$^4$ is hydrogen, halogen, methyl, halomethyl or cyano;
R$^5$ is hydrogen;
or R$^4$ and R$^5$ together form a bridging 1,3-butadiene group;
p is 2 or 3.

In a further aspect the invention provides use of a compound of formula I for the control of a soil-dwelling pest in useful plants.

Preferably the soil-dwelling pest is selected from corn rootworm, wireworms, grubs, in particular white grubs (e.g. *Phyllophaga* sp., *Diloboderus* sp., *Popillia japonica*), termites (in particular for sugar cane), subterraneous stinkbugs (e.g. *Scaptocoris* sp.), cutworms (e.g. *agrotis* sp.), millipedes (e.g. *Julus* sp.) and broca gigante (e.g. *Telchin licus*).

In one embodiment the invention provides a method of controlling and/or preventing corn rootworm in useful plants comprising applying to the locus of the useful plant or treating plant propagation material thereof, preferably a seed, with a compound of formula I.

In one embodiment the invention provides a method of controlling and/or preventing wireworms in useful plants comprising applying to the locus of the useful plant or treating plant propagation material thereof, preferably a seed, with a compound of formula I.

In one embodiment the invention provides a method of controlling and/or preventing grubs, in particular white grubs, in useful plants comprising applying to the locus of the useful plant or treating plant propagation material thereof, preferably a seed, with a compound of formula I.

In one embodiment the invention provides a method of controlling and/or preventing *Phyllophaga* sp. in useful plants comprising applying to the locus of the useful plant or treating plant propagation material thereof, preferably a seed, with a compound of formula I.

In one embodiment the invention provides a method of controlling and/or preventing *Diloboderus* sp. in useful plants comprising applying to the locus of the useful plant or treating plant propagation material thereof, preferably a seed, with a compound of formula I.

In one embodiment the invention provides a method of controlling and/or preventing *Popillia japonica* in useful plants comprising applying to the locus of the useful plant or treating plant propagation material thereof, preferably a seed, with a compound of formula I.

In one embodiment the invention provides a method of controlling and/or preventing termites (in particular for sugar cane) in useful plants comprising applying to the locus of the useful plant or treating plant propagation material thereof, preferably a seed, with a compound of formula I.

In one embodiment the invention provides a method of controlling and/or preventing subterraneous stinkbugs (e.g. *Scaptocoris* sp.) in useful plants comprising applying to the locus of the useful plant or treating plant propagation material thereof, preferably a seed, with a compound of formula I.

In one embodiment the invention excludes a method of controlling and/or preventing stinkbugs.

In one embodiment the invention provides a method of controlling and/or preventing cutworms (e.g. *agrotis* sp.) in useful plants comprising applying to the locus of the useful plant or treating plant propagation material thereof, preferably a seed, with a compound of formula I.

In one embodiment the invention provides a method of controlling and/or preventing millipedes (e.g. *Julus* sp.) in useful plants comprising applying to the locus of the useful plant or treating plant propagation material thereof, preferably a seed, with a compound of formula I.

In one embodiment the invention provides a method of controlling and/or preventing broca gigante (e.g. *Telchin licus*) in useful plants comprising applying to the locus of the useful plant or treating plant propagation material thereof, preferably a seed, with a compound of formula I.

In a further aspect the invention provides a method of improving the growth of useful plants comprising applying to the locus of the useful plant or treating plant propagation material thereof, preferably a seed, with a compound of formula I.

In a further aspect the invention provides use of a compound of formula I for improving the growth of useful plants.

In a further aspect the invention provides a method comprising applying a compound of formula I to the locus of corn plants by direct soil application. Preferred compounds are described below, preferably $B^1$—$B^2$—$B^3$— is —C=N—O—, $A^1$ and $A^2$ are C—H, $R^2$ is trifluoromethyl, $R^3$ is chloro or fluoro, $R^4$ is halogen or methyl, $R^5$ is hydrogen, L is a direct bond and most preferably $R^1$ is ethyl or trifluoroethyl.

In a further aspect the invention provides a method of controlling and/or preventing corn rootworm in corn plants comprising applying a compound of formula I to the locus of corn plants by direct soil application. Preferred compounds are described below, preferably $B^1$—$B^2$—$B^3$— is —C=N—O—, $A^1$ and $A^2$ are C—H, $R^2$ is trifluoromethyl, each $R^3$ is independently chloro or fluoro, $R^4$ is halogen or methyl, $R^5$ is hydrogen, L is a direct bond and most preferably $R^1$ is ethyl or trifluoroethyl.

In a further aspect the invention provides a method comprising applying a compound of formula I to the locus of corn plants by in-furrow application. Preferred compounds are described below, preferably $B^1$—$B^2$—$B^3$— is —C=N—O—, $A^1$ and $A^2$ are C—H, $R^2$ is trifluoromethyl, each $R^3$ is independently chloro or fluoro, $R^4$ is halogen or methyl, $R^5$ is hydrogen, L is a direct bond and most preferably $R^1$ is ethyl or trifluoroethyl.

In a further aspect the invention provides a method of controlling and/or preventing corn rootworm in corn plants comprising applying a compound of formula I to the locus of corn plants by direct soil application. Preferred compounds are described below, preferably $B^1$—$B^2$—$B^3$— is —C=N—O—, $A^1$ and $A^2$ are C—H, $R^2$ is trifluoromethyl, each $R^3$ is independently chloro or fluoro, $R^4$ is halogen or methyl, $R^5$ is hydrogen, L is a direct bond and most preferably $R^1$ is ethyl or trifluoroethyl.

In a further aspect the invention provides a method of controlling and/or preventing corn rootworm in corn plants comprising applying a compound of formula I to the locus of corn plants by in-furrow application. Preferred compounds are described below, preferably $B^1$—$B^2$—$B^3$— is —C=N—O—, $A^1$ and $A^2$ are C—H, $R^2$ is trifluoromethyl, each $R^3$ is independently chloro or fluoro, $R^4$ is halogen or methyl, $R^5$ is hydrogen, L is a direct bond and most preferably $R^1$ is ethyl or trifluoroethyl.

In a further aspect the invention provides a method of controlling and/or preventing corn rootworm in useful plants comprising applying a compound of formula I to the locus of the useful plants by direct soil application. Preferred compounds are described below, preferably $B^1$—$B^2$—$B^3$— is —C=N—O—, $A^1$ and $A^2$ are C—H, $R^2$ is trifluoromethyl, each $R^3$ is independently chloro or fluoro, $R^4$ is halogen or methyl, $R^5$ is hydrogen, L is a direct bond and most preferably $R^1$ is ethyl or trifluoroethyl.

In a further aspect the invention provides a method of controlling and/or preventing corn rootworm in useful plants comprising applying a compound of formula I to the locus of the useful plants by in-furrow application. Preferred compounds are described below, preferably $B^1$—$B^2$—$B^3$— is —C=N—O—, $A^1$ and $A^2$ are C—H, $R^2$ is trifluoromethyl, each $R^3$ is independently chloro or fluoro, $R^4$ is halogen or methyl, $R^5$ is hydrogen, L is a direct bond and most preferably $R^1$ is ethyl or trifluoroethyl.

In a further aspect the invention provides use of a compound of formula I for controlling and/or preventing corn rootworm in useful plants, preferably corn plants, by applying a compound of formula I to the locus of the useful plants directly to soil. Preferred compounds are described below, preferably $B^1$—$B^2$—$B^3$— is —C=N—O—, $A^1$ and $A^2$ are C—H, $R^2$ is trifluoromethyl, each $R^3$ is independently chloro or fluoro, $R^4$ is halogen or methyl, $R^5$ is hydrogen, L is a direct bond and most preferably $R^1$ is ethyl or trifluoroethyl.

In a further aspect the invention provides use of a compound of formula I for controlling and/or preventing corn rootworm by applying a compound of formula I to the locus of the useful plants and applying the compound of formula I by in-furrow application. Preferred compounds are described below, preferably $B^1$—$B^2$—$B^3$— is —C=N—O—, $A^1$ and $A^2$ are C—H, $R^2$ is trifluoromethyl, each $R^3$ is independently chloro or fluoro, $R^4$ is halogen or methyl, $R^5$ is hydrogen, L is a direct bond and most preferably $R^1$ is ethyl or trifluoroethyl.

In a further aspect the invention provides a method comprising applying a compound of formula I to a field of corn plants, before, during or after planting, and wherein the application of the compound of formula I comprises applying the compound of formula I directly to soil. Preferred compounds are described below, preferably $B^1$—$B^2$—$B^3$— is —C=N—O—, $A^1$ and $A^2$ are C—H, $R^2$ is trifluoromethyl, each $R^3$ is independently chloro or fluoro, $R^4$ is halogen or methyl, $R^5$ is hydrogen, L is a direct bond and most preferably $R^1$ is ethyl or trifluoroethyl.

In a further aspect the invention provides a method comprising applying a compound of formula I to a field of corn plants, before, during or after planting, and wherein the application of the compound of formula I comprises applying the compound of formula I by in-furrow application. Preferred compounds are described below, preferably $B^1$—$B^2$—$B^3$— is —C=N—O—, $A^1$ and $A^2$ are C—H, $R^2$ is trifluoromethyl, each $R^3$ is independently chloro or fluoro, $R^4$ is halogen or methyl, $R^5$ is hydrogen, L is a direct bond and most preferably $R^1$ is ethyl or trifluoroethyl.

In a further aspect the invention provides a method of controlling and/or preventing corn rootworm in corn plants comprising applying a compound of formula I to a field of corn plants, before, during or after planting, and wherein the application of the compound of formula I comprises applying the compound of formula I directly to soil. Preferred compounds are described below, preferably $-B^1-B^2-B^3-$ is $-C=N-O-$, $A^1$ and $A^2$ are C—H, $R^2$ is trifluoromethyl, each $R^3$ is independently chloro or fluoro, $R^4$ is halogen or methyl, $R^5$ is hydrogen, L is a direct bond and most preferably $R^1$ is ethyl or trifluoroethyl.

In a further aspect the invention provides a method of controlling and/or preventing corn rootworm in corn plants comprising applying a compound of formula I to a field of corn plants, before, during or after planting, and wherein the application of the compound of formula I comprises applying the compound of formula I by in-furrow application. Preferred compounds are described below, preferably $B^1-B^2-B^3-$ is $-C=N-O-$, $A^1$ and $A^2$ are C—H, $R^2$ is trifluoromethyl, each $R^3$ is independently chloro or fluoro, $R^4$ is halogen or methyl, $R^5$ is hydrogen, L is a direct bond and most preferably $R^1$ is ethyl or trifluoroethyl.

Application before planning includes e.g. up to 1, 2, 3, 4, 5, or even up to 10 days before planting. Application after planting includes e.g. up to 1, 2, 3, 4, 5, or even up to 10 days after planting. For example application may be up to 10 days before or after planting, preferably up to 5 days before or after planting, more preferably up to 2 days before or after planting, most preferably up to 1 day before or after planting.

Seed treatment is an example of indirect application to soil, e.g. the application of the compound of formula I directly to soil comprises applying the compound of formula I to the soil other than via seed treatment.

In a further aspect, the invention provides a method for obtaining regulatory approval for the use of one or more of a compound of formula I to control a pest selected from corn rootworm, wireworms, grubs, in particular white grubs, termites, subterraneous stinkbugs, cutworms, millipedes and broca gigante, comprising at least one step of referring to, submitting or relying on biological data showing that said active ingredient reduces insect pressure.

Use of the compounds of the invention against wireworms is particularly preferred.

The compounds of formula (I) may exist in different geometric or optical isomers or tautomeric forms. This invention covers all such isomers and tautomers and mixtures thereof in all proportions as well as isotopic forms such as deuterated compounds. The invention also covers salts and N-oxides of the compounds of the invention.

Preferred substituent definitions are described below and may be combined in any combination, including with original definitions.

$-B^1-B^2-B^3-$ is preferably $-C=N-O-$.

$A^1$ and $A^2$ are preferably C—H.

Preferably $X^1$ is 3,5-dichlorophenyl-, 3-chloro-4-fluorophenyl-, 3-fluoro-4-chlorophenyl-, 3,4-dichlorophenyl-, 3-chloro-4-bromophenyl-, 3,5-dichloro-4-fluorophenyl-, 3,4,5-trichlorophenyl-, 3,4,5-trifluorophenyl-, 3-chloro-5-bromophenyl-, 3-chloro-5-fluorophenyl-, 3-chloro-5-(trifluoromethyl)phenyl-, 3,4-dichloro-5-(trifluoromethyl)phenyl-, 3,5-bis(trifluoromethyl)phenyl-, 4-chloro-3,5-bis(trifluoromethyl)phenyl-, 3-(trifluoromethyl)phenyl, more preferably 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 3,5-dichloro-4-bromophenyl-, 3-bromo-5-(trifluoromethyl)phenyl-, 3,5-dibromophenyl-, or 3,4-dichlorophenyl-, even more preferably 3,5-dichloro-phenyl, 3,5-dichloro-4-fluorophenyl-, 3,4,5-trichlorophenyl-, 3,5-bis(trifluoromethyl)phenyl, most preferably $R^4$ is 3,5-dichloro-phenyl.

$R^1$ is preferably methyl, ethyl, propyl, butyl, cyclopropyl, cyclobutyl, trifluoroethyl, difluoroethyl. Ethyl and trifluoroethyl are particularly preferred.

$R^2$ is preferably trifluoromethyl.

Preferably each $R^3$ is independently chlorine or fluorine, most preferably chlorine.

$R^4$ is preferably chloro or methyl, most preferably methyl.

$R^5$ is preferably hydrogen.

L is preferably a direct bond.

In one group of compounds $-B^1-B^2-B^3-$ is $-C=N-O-$.

In one group of compounds $-B^1-B^2-B^3-$ is $-C=N-CH_2-$.

In one group of compounds $-B^1-B^2-B^3-$ is $-C=CH_2-O-$.

In one group of compounds $-B^1-B^2-B^3-$ is $-N-CH_2-CH_2-$.

In one embodiment $A^1$ and $A^2$ are C—H, $R^2$ is trifluoromethyl, and $R^5$ is hydrogen.

In one embodiment $A^1$ and $A^2$ are C—H, $R^2$ is trifluoromethyl, $R^5$ is hydrogen and L is a direct bond.

In one embodiment $-B^1-B^2-B^3-$ is $-C=N-O-$, $A^1$ and $A^2$ are C—H, $R^2$ is trifluoromethyl, $R^5$ is hydrogen and L is a direct bond.

In one embodiment $-B^1-B^2-B^3-$ is $-C=N-O-$, $A^1$ and $A^2$ are C—H, $R^2$ is trifluoromethyl, $R^4$ is halogen or methyl, $R^5$ is hydrogen and L is a direct bond.

In one embodiment $-B^1-B^2-B^3-$ is $-C=N-O-$, $A^1$ and $A^2$ are C—H, $R^2$ is trifluoromethyl, $R^3$ is chloro or fluoro, $R^4$ is halogen or methyl, $R^5$ is hydrogen and L is a direct bond.

In one embodiment $A^1$ and $A^2$ are C—H, $R^2$ is trifluoromethyl, $R^4$ is methyl, $R^5$ is hydrogen, each $R^3$ is chlorine, p is 2.

In one embodiment $R^1$ is $C_1$-$C_4$alkyl, e.g. methyl, ethyl or propyl, e.g. methyl or ethyl, e.g. ethyl.

In one embodiment $X^1$ is group Xa

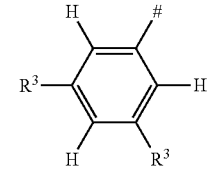

Xa

In one embodiment $R^1$ is $C_1$-$C_8$alkyl, e.g. methyl, ethyl or propyl, e.g. methyl or ethyl, e.g. ethyl and $X^1$ is group Xa.

In one embodiment $R^1$ is methyl.

In one embodiment $R^1$ is ethyl.

In one embodiment $R^1$ is 2,2,2-trifluoroethyl.

In one embodiment $R^1$ is 2,2-difluoroethyl.

In one embodiment $X^1$ is 3,5-dichlorophenyl.

In one embodiment $X^1$ is 3,5-dichloro-4-fluorophenyl.

In one embodiment $X^1$ is 3,4,5-trichlorophenyl.

In one embodiment $R^1$ is methyl and $X^1$ is 3,5-dichlorophenyl.

In one embodiment $R^1$ is methyl and $X^1$ is 3,5-dichloro-4-fluorophenyl.

In one embodiment $R^1$ is methyl and $X^1$ is 3,4,5-trichlorophenyl.

In one embodiment $R^1$ is ethyl and $X^1$ is 3,5-dichlorophenyl.

In one embodiment $R^1$ is ethyl and $X^1$ is 3,5-dichloro-4-fluorophenyl.

In one embodiment $R^1$ is ethyl and $X^1$ is 3,4,5-trichlorophenyl.

In one embodiment $R^1$ is 2,2,2-trifluoroethyl and $X^1$ is 3,5-dichlorophenyl.

In one embodiment $R^1$ is 2,2,2-trifluoroethyl and $X^1$ is 3,5-dichloro-4-fluorophenyl.

In one embodiment $R^1$ is 2,2,2-trifluoroethyl and $X^1$ is 3,4,5-trichlorophenyl.

In one embodiment $R^1$ is 2,2-difluoroethyl and $X^1$ is 3,5-dichlorophenyl.

In one embodiment $R^1$ is 2,2-difluoroethyl and $X^1$ is 3,5-dichloro-4-fluorophenyl.

In one embodiment $R^1$ is 2,2-difluoroethyl and $X^1$ is 3,4,5-trichlorophenyl.

Compounds of formula I may exist as compounds of formula I* or compounds of formula I**.

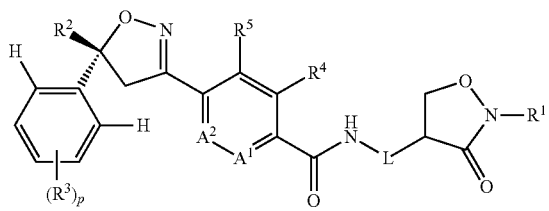
(I*)

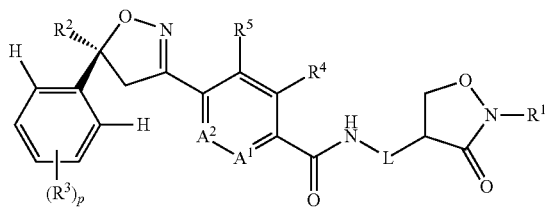
(I**)

Compounds of formula I** are more biologically active than compounds of formula I*. Compounds of formula I may be a mixture of compounds I* and I in any ratio e.g. in a molar ratio of 1:99 to 99:1, e.g. 10:1 to 1:10, e.g. a substantially 50:50 molar ratio. Preferably the compound of formula I is a racemic mixture of the compounds of formula I and I* or is enantiomerically enriched for the compound of formula I. For example, when the compound of formula I is an enantiomerically enriched mixture of formula I, the molar proportion of compound I compared to the total amount of both enantiomers is for example greater than 50%, e.g. at least 55, 60, 65, 70, 75, 80, 85, 90, 95, 96, 97, 98, or at least 99%. In one embodiment the compound of formula I is a compound of formula I in substantially pure form, e.g. it is provided substantially in the absence of the alternative enantiomer.

Compounds of formula I may also exist as compounds of formula I' or compounds of formula I".

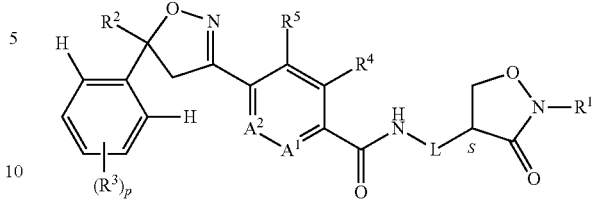
(I')

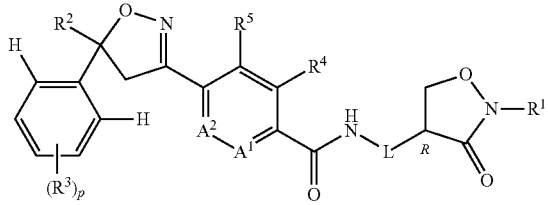
(I")

(S=S stereochemistry, R=R stereochemistry)

Compounds of formula I" are often more biologically active than compounds of formula I'. The compound of formula I may be a mixture of compounds I' and I" in any ratio e.g. in a molar ratio of 1:99 to 99:1, e.g. 10:1 to 1:10, e.g. a substantially 50:50 molar ratio. Preferably the compound of formula I is a racemic mixture of the compounds of formula I" and I' or is enantiomerically enriched for the compound of formula I". For example, when the compound of formula I is an enantiomerically enriched mixture of formula I", the molar proportion of compound I" compared to the total amount of both enantiomers is for example greater than 50%, e.g. at least 55, 60, 65, 70, 75, 80, 85, 90, 95, 96, 97, 98, or at least 99%. In a preferred embodiment the compound of formula I is a compound of formula I" in substantially pure form, e.g. it is provided substantially in the absence of the alternative enantiomer.

The above stereocentres give rise to four stereoisomers:

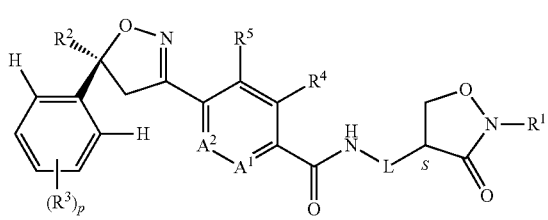
(I-i)

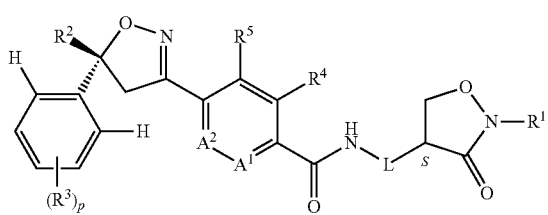
(I-ii)

-continued

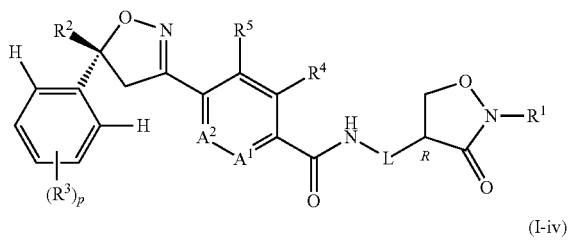
(I-iii)

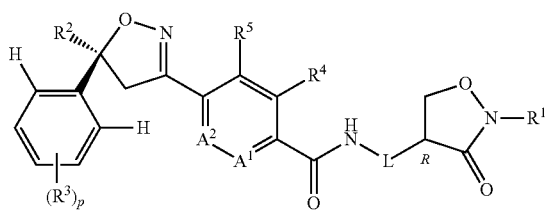
(I-iv)

In one embodiment the compound of formula I is a mixture comprising compounds I-i, I-ii, I-iii and I-iv, wherein the mixture is enriched for the compound of formula I-iv, e.g. the molar proportion of compound I-iv compared to the total amount of the four isomers is for example greater than 25%, e.g. at least 30, 35, 40, 50 55, 60, 65, 70, 75, 80, 85, 90, 95, 96, 97, 98, or at least 99%.

In another embodiment the compound of formula I is a mixture comprising compounds I-i, I-ii, I-iii and I-iv, wherein the molar amount of the compound of formula I-iv is greater than the molar amount of the compound of formula I-i, and the molar amount of the compound I-ii, and the molar amount of the compound of formula I-iii, in other words, the compound of formula I-iv is the most abundant isomer in the mixture. For example the molar amount of compound of formula I-iv is at least 1, 2, 5, 10, 15, 20, 25, 30, 35, 40, 45, 50, 55, 60, 56, 70, 75, 80, 85, 90, or even at least 95% greater than the combined amount of the compound of formula I-iv and I-i, the combined amount of the compound of formula I-iv and I-ii, and the combined amount of the compound of formula I-iv and I-iii.

Although $B^1$—$B^2$—$B^3$ is shown above as C=N—O, the same applies in respect of the stereoisomers when $B^1$—$B^2$—$B^3$ is —C=N—$CH_2$—, —C=$CH_2$—O— and —N—$CH_2$—$CH_2$—.

In one embodiment the compound of formula I-iv is the most abundant isomer and $R^1$ is $C_1$-$C_4$alkyl, e.g. methyl, ethyl or propyl, e.g. methyl or ethyl, e.g. ethyl.

In one embodiment the compound of formula I-iv is the most abundant isomer and $R^1$ is $C_1$-$C_4$alkyl, e.g. methyl, ethyl or propyl, e.g. methyl or ethyl, e.g. ethyl and $X^1$ is group Xa.

In one embodiment the compound of formula I-iv is the most abundant isomer and $R^1$ is methyl.

In one embodiment the compound of formula I-iv is the most abundant isomer and $R^1$ is ethyl.

In one embodiment the compound of formula I-iv is the most abundant isomer and $R^1$ is 2,2,2-trifluoroethyl.

In one embodiment the compound of formula I-iv is the most abundant isomer and $R^1$ is 2,2-difluoroethyl.

In all embodiments of the invention the method is preferably a method of controlling and/or preventing infestation of wireworms in (a crop of) useful plants.

Preferred compounds of formula I are shown in the Tables below.

TABLE A

Compounds of formula (I-a)

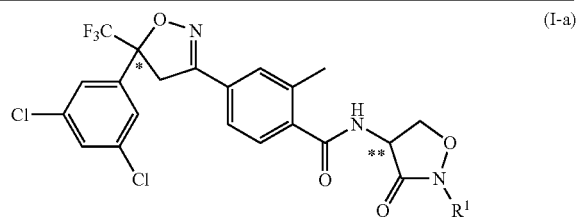
(I-a)

Table A provides 78 compounds and mixtures of formula (I-a) wherein $R^1$ has the values listed in table X below. The symbols * and ** indicate the location of the chiral centres.

TABLE B

Compounds of formula (I-b)

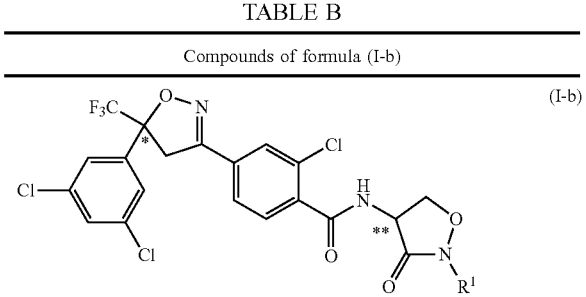
(I-b)

Table B provides 78 compounds and mixtures of formula (I-b) wherein $R^1$ has the values listed in table X below. The symbols * and ** indicate the location of the chiral centres.

TABLE C

Compounds of formula (I-c)

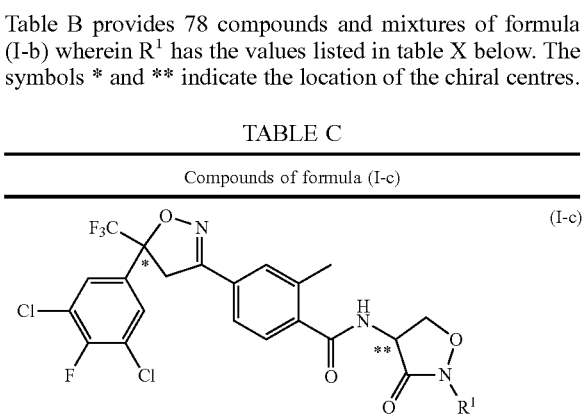
(I-c)

Table C provides 78 compounds and mixtures of formula (I-c) wherein $R^1$ has the values listed in table X below. The symbols * and ** indicate the location of the chiral centres.

TABLE D

Compounds of formula (I-d)

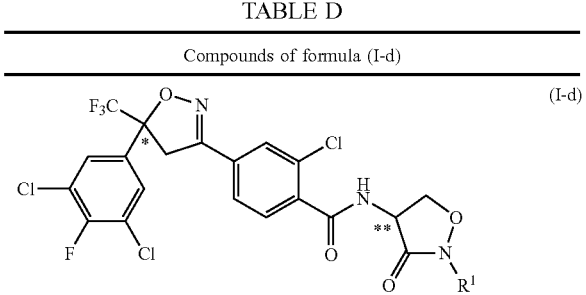
(I-d)

Table D provides 78 compounds and mixtures of formula (I-d) wherein $R^1$ has the values listed in table X below. The symbols * and ** indicate the location of the chiral centres.

TABLE E

Compounds of formula (I-e)

(I-e) [structure: F₃C-substituted isoxazoline with 3,4,5-trichlorophenyl group, connected via methyl-substituted phenyl to amide-isoxazolidinone bearing R¹]

Table E provides 78 compounds and mixtures of formula (I.e) wherein R¹ has the values listed in table X below. The symbols * and ** indicate the location of the chiral centres.

TABLE F

Compounds of formula (I-f)

(I-f) [structure: F₃C-substituted isoxazoline with 3,4,5-trichlorophenyl group, connected via chloro-substituted phenyl to amide-isoxazolidinone bearing R¹]

Table F provides 78 compounds and mixtures of formula (I-f) wherein R¹ has the values listed in table X below. The symbols * and ** indicate the location of the chiral centres.

Table X represents Table A when X is A, Table B when X is B, Table C when X is C, Table D when X is D, Table E when X is E, Table F when X is F.

| Compound numbers | Stereochemistry at * | Stereochemistry at ** | R¹ |
|---|---|---|---|
| X.1 | Racemic mixture | Racemic mixture | ethyl- |
| X.2 | Racemic mixture | Racemic mixture | butyl- |
| X.3 | Racemic mixture | Racemic mixture | but-2-yl- |
| X.4 | Racemic mixture | Racemic mixture | 3-bromo-propyl- |
| X.5 | Racemic mixture | Racemic mixture | 2,2,2-trifluoro-ethyl- |
| X.6 | Racemic mixture | Racemic mixture | 3,3,3-trifluoro-propyl- |
| X.7 | Racemic mixture | Racemic mixture | cyclobutyl- |
| X.8 | Racemic mixture | Racemic mixture | methyl |
| X.9 | Racemic mixture | Racemic mixture | propyl |
| X.10 | Racemic mixture | Racemic mixture | 2,2-difluoro-ethyl- |
| X.11 | Racemic mixture | Racemic mixture | 2-fluoro-ethyl- |
| X.12 | S | Racemic mixture | ethyl- |
| X.13 | S | Racemic mixture | butyl- |
| X.14 | S | Racemic mixture | but-2-yl- |
| X.15 | S | Racemic mixture | 3-bromo-propyl- |
| X.16 | S | Racemic mixture | 2,2,2-trifluoro-ethyl- |
| X.17 | S | Racemic mixture | 3,3,3-trifluoro-propyl- |
| X.18 | S | Racemic mixture | cyclobutyl- |
| X.19 | S | Racemic mixture | methyl |
| X.20 | S | Racemic mixture | propyl |
| X.21 | S | Racemic mixture | 2,2-difluoro-ethyl- |
| X.22 | S | Racemic mixture | 2-fluoro-ethyl- |
| X.23 | Racemic mixture | Racemic mixture | isopropyl |
| X.24 | Racemic mixture | Racemic mixture | cyclopropyl |
| X.25 | S | Racemic mixture | isopropyl |
| X.26 | S | Racemic mixture | cyclopropyl |
| X.27 | Racemic mixture | S | ethyl- |
| X.28 | Racemic mixture | S | butyl- |
| X.29 | Racemic mixture | S | but-2-yl- |
| X.30 | Racemic mixture | S | 3-bromo-propyl- |
| X.31 | Racemic mixture | S | 2,2,2-trifluoro-ethyl- |
| X.32 | Racemic mixture | S | 3,3,3-trifluoro-propyl- |
| X.33 | Racemic mixture | S | cyclobutyl- |
| X.34 | Racemic mixture | S | methyl |
| X.35 | Racemic mixture | S | propyl |
| X.36 | Racemic mixture | S | 2,2-difluoro-ethyl- |
| X.37 | Racemic mixture | S | 2-fluoro-ethyl- |
| X.38 | S | S | ethyl- |
| X.39 | S | S | butyl- |
| X.40 | S | S | but-2-yl- |
| X.41 | S | S | 3-bromo-propyl- |
| X.42 | S | S | 2,2,2-trifluoro-ethyl- |
| X.43 | S | S | 3,3,3-trifluoro-propyl- |
| X.44 | S | S | cyclobutyl- |
| X.45 | S | S | methyl |
| X.46 | S | S | propyl |
| X.47 | S | S | 2,2-difluoro-ethyl- |
| X.48 | S | S | 2-fluoro-ethyl- |
| X.49 | Racemic mixture | S | isopropyl |
| X.50 | Racemic mixture | S | cyclopropyl |
| X.51 | S | S | isopropyl |
| X.52 | S | S | cyclopropyl |
| X.53 | Racemic mixture | R | ethyl- |
| X.54 | Racemic mixture | R | butyl- |
| X.55 | Racemic mixture | R | but-2-yl- |
| X.56 | Racemic mixture | R | 3-bromo-propyl- |
| X.57 | Racemic mixture | R | 2,2,2-trifluoro-ethyl- |
| X.58 | Racemic mixture | R | 3,3,3-trifluoro-propyl- |
| X.59 | Racemic mixture | R | cyclobutyl- |
| X.60 | Racemic mixture | R | methyl |
| X.61 | Racemic mixture | R | propyl |
| X.62 | Racemic mixture | R | 2,2-difluoro-ethyl- |
| X.63 | Racemic mixture | R | 2-fluoro-ethyl- |
| X.64 | S | R | ethyl- |
| X.65 | S | R | butyl- |
| X.66 | S | R | but-2-yl- |
| X.67 | S | R | 3-bromo-propyl- |
| X.68 | S | R | 2,2,2-trifluoro-ethyl- |
| X.69 | S | R | 3,3,3-trifluoro-propyl- |
| X.70 | S | R | cyclobutyl- |
| X.71 | S | R | methyl |
| X.72 | S | R | propyl |
| X.73 | S | R | 2,2-difluoro-ethyl- |
| X.74 | S | R | 2-fluoro-ethyl- |
| X.75 | Racemic mixture | R | isopropyl |
| X.76 | Racemic mixture | R | cyclopropyl |
| X.77 | S | R | isopropyl |
| X.78 | S | R | cyclopropyl |

The compounds of the invention may be made by a variety of methods as shown in Schemes 1 to 3.

Scheme 1

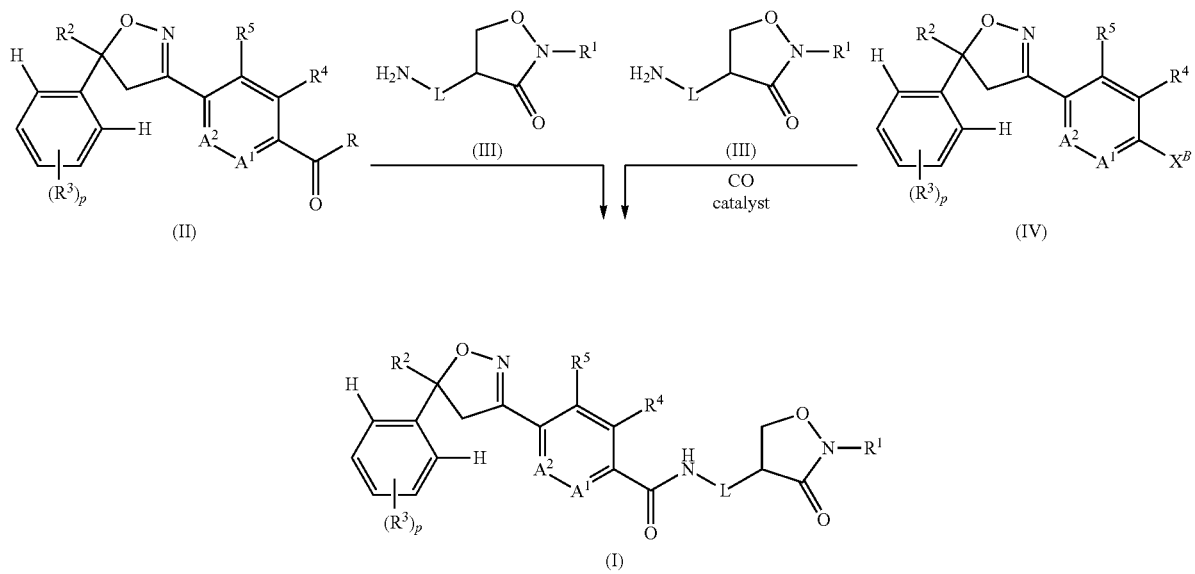

1) Compounds of formula (I), can be prepared by reacting a compound of formula (II) wherein R is OH, $C_1$-$C_6$alkoxy or Cl, F or Br, with an amine of formula (III) as shown in Scheme 1. When R is OH such reactions are usually carried out in the presence of a coupling reagent, such as N,N'-dicyclohexyl-carbodiimide ("DCC"), 1-ethyl-3-(3-dimethylamino-propyl)carbodiimide hydrochloride ("EDC") or bis (2-oxo-3-oxazolidinyl)phosphonic chloride ("BOP-Cl"), in the presence of a base, and optionally in the presence of a nucleophilic catalyst, such as hydroxybenzotriazole ("HOBT"). When R is Cl, such reactions are usually carried out in the presence of a base, and optionally in the presence of a nucleophilic catalyst. Alternatively, it is possible to conduct the reaction in a biphasic system comprising an organic solvent, preferably ethyl acetate, and an aqueous solvent, preferably a solution of sodium hydrogen carbonate. When R is $C_1$-$C_6$alkoxy it is sometimes possible to convert the ester directly to the amide by heating the ester and amine together in a thermal process. Suitable bases include pyridine, triethylamine, 4-(dimethylamino)-pyridine ("DMAP") or diisopropylethylamine (Hunig's base). Preferred solvents are N,N-dimethylacetamide, tetrahydrofuran, dioxane, 1,2-dimethoxyethane, ethyl acetate and toluene. The reaction is carried out at a temperature of from 0° C. to 100° C., preferably from 15° C. to 30° C., in particular at ambient temperature Amines of formula (III) are either known in the literature or can be prepared using methods known to a person skilled in the art.

2) Acid halides of formula (II), wherein R is Cl, F or Br, may be made from carboxylic acids of formula (II), wherein R is OH, under standard conditions, as described for example in WO 2009/080250.

3) Carboxylic acids of formula (II), wherein R is OH, may be formed from esters of formula (II), wherein R is $C_1$-$C_6$alkoxy as described for example in WO 2009/080250.

4) Compounds of formula (I) can be prepared by reacting a compound of formula (IV) wherein $X^B$ is a leaving group, for example a halogen, such as bromo, with carbon monoxide and an amine of formula (III), in the presence of a catalyst, such as palladium(II) acetate or bis-(triphenylphosphine)palladium(II) dichloride, optionally in the presence of a ligand, such as triphenylphosphine, and a base, such as sodium carbonate, pyridine, triethylamine, 4-(dimethylamino)-pyridine ("DMAP") or diisopropylethylamine (Hunig's base), in a solvent, such as water, N,N-dimethylformamide or tetrahydrofuran. The reaction is carried out at a temperature of from 50° C. to 200° C., preferably from 100° C. to 150° C. The reaction is carried out at a pressure of from 50 to 200 bar, preferably from 100 to 150 bar.

5) Compounds of formula (IV) wherein $X^B$ is a leaving group, for example a halogen, such as bromo, can be made by a various of methods, for example as described in WO 2009/080250.

Scheme 2

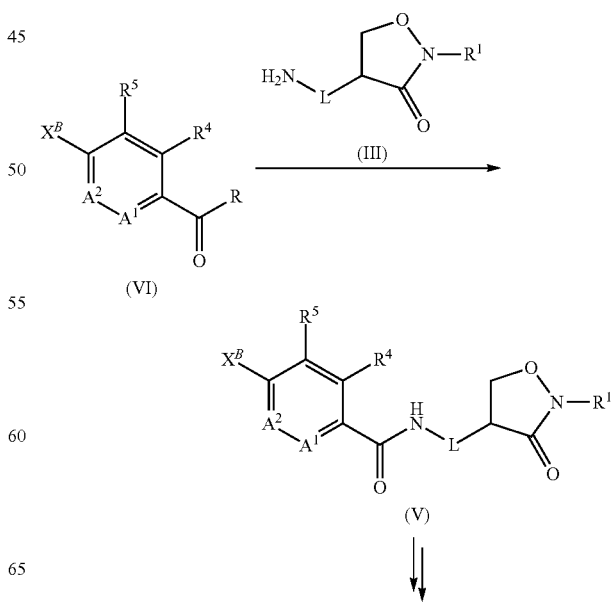

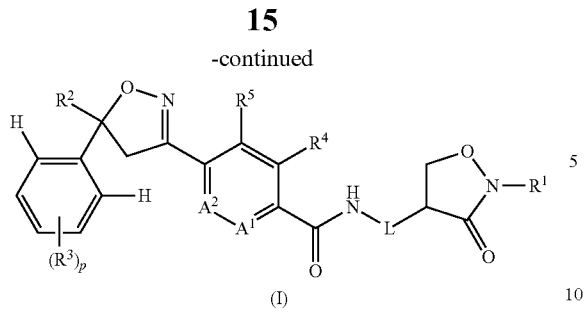

(I)

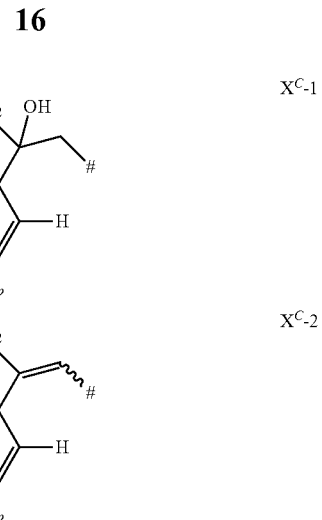

6) Alternatively, compounds of formula (I), can be prepared by various methods from an intermediate of formula (V) as shown in Scheme 2 wherein $X^B$ is a leaving group, for example a halogen, such as bromo, or $X^B$ is cyano, formyl or acetyl according to similar methods to those described in WO09080250. An intermediate of formula (V) can be prepared for example from an intermediate of formula (VI) as described in the same reference.

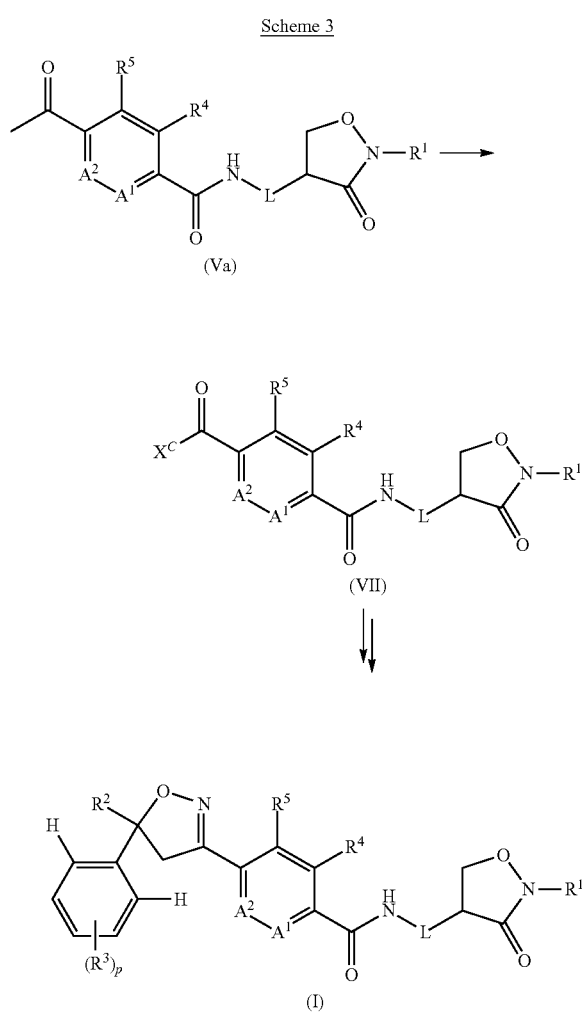

7) Alternatively, compounds of formula (I) can be prepared by various methods from an intermediate of formula (VII) as shown in Scheme 3 wherein $X^C$ is $X^C$-1 or $X^C$-2 according to similar methods to those described in WO2009/080250.

8) Compounds of formula (VII) wherein $X^C$ is $X^C$ is $X^C$-1 or $X^C$-2 can be prepared from a compound of formula (Va) from a compound of formula (VII) wherein $X^C$ is $CH_2$-halogen using similar methods to those described in WO2009/080250.

9) Compounds of formula (VII) wherein $X^C$ is $CH_2$-halogen, such as bromo or chloro, can be prepared by reacting a methyl ketone of formula (Va) with a halogenating agent, such as bromine or chlorine, in a solvent, such as acetic acid, at a temperature of from 0° C. to 50° C., preferably from ambient temperature to 40° C.

Other methods for the preparation of compounds of formula I are described in PCT/EP2010/068605, which is incorporated herein by reference.

The term "soil-dwelling pest" refers to a pest that causes plant damage whilst in a life cycle phase that lives in the soil, and for example, damages plant roots. Examples of specific pests are described below. Soil dwelling pests may be insects, acarines and/or nematodes, preferably insects, or acarines, most preferably insects.

In one embodiment the invention provides a compound selected from Tables A to F for use in controlling and/or preventing soil pests.

In one embodiment the invention provides a compound selected from Tables A to F for use in controlling and/or preventing corn rootworm.

In one embodiment the invention provides a compound selected from Tables A to F for use in controlling and/or preventing wireworms (preferred).

In one embodiment the invention provides a compound selected from Tables A to F for use in controlling and/or preventing grubs, in particular white grubs.

In one embodiment the invention provides a compound selected from Tables A to F for use in controlling and/or preventing *Phyllophaga* sp.

In one embodiment the invention provides a compound selected from Tables A to F for use in controlling and/or preventing *Diloboderus* sp.

In one embodiment the invention provides a compound selected from Tables A to F for use in controlling and/or preventing *Popillia japonica*.

In one embodiment the invention provides a compound selected from Tables A to F for use in controlling and/or preventing termites, e.g. for sugarcane.

In one embodiment the invention provides a compound selected from Tables A to F for use in controlling and/or preventing subterraneous stinkbugs, e.g. *Scaptocoris* sp.

In one embodiment the invention provides a compound selected from Tables A to F for use in controlling and/or preventing cutworms, e.g. *agrotis* sp.

In one embodiment the invention provides a compound selected from Tables A to F for use in controlling and/or preventing millipedes, e.g. *Julus* sp.

In one embodiment the invention provides a compound selected from Tables A to F for use in controlling and/or preventing broca gigante, e.g. *Telchin licus*.

In one embodiment the compounds of formula (I), in particular those in Tables A to F above may be used to combat soil grubs e.g. *Migdolus* sp.; *Phyllophaga* sp.; *Diloboderus* sp.; *Cyclocephala* sp; *Lyogenys fuscus*; *Popillia japonica*; sugar cane weevils e.g. *Sphenophorus levis* and *Metamasius hemipterus*; termites e.g. *Heterotermes tenuis*; *Heterotermes longiceps*; *Cornitermes cumulans*; *Procornitermes triacifer*; *Neocapritermes opacus*; *Neocapritermes parvus*; corn rootworms e.g. *Diabrotica* sp., seed Maggot e.g. *Delia platura*; soil stinkbugs e.g. *Scaptocoris castanea*; wireworms e.g. *Agriotes* sp.; *Athous* sp.; *Hipnodes bicolor*; *Ctenicera destructor*; *Limonius canu*; *Limonius californicus*.

In another embodiment the compounds of formula (I), in particular those in Tables A to F above may be used for seed applications at least on the following: soil grubs for corn, soybeans, sugarcane: e.g. *Migdolus* sp.; *Phyllophaga* sp.; *Diloboderus* sp.; *Cyclocephala* sp.; *Lyogenys fuscus*; *Popillia japonica*; termites for soybeans, sugarcane, pasture: e.g. *Heterotermes tenuis*; *Heterotermes longiceps*; *Cornitermes cumulans*; *Procornitermes triacifer*; *Neocapritermes opacus*; *Neocapritermes parvus*; corn rootworms for corn and potatoes: e.g. *Diabrotica* sp., rice water weevil e.g. *Lissorhoptrus oryzophilus*; red legged earth mites e.g. *Halotydeus destructor*.

In one embodiment the compounds of formula (I), in particular those in Tables A to F above, may be used for soil applications, including as a seed application, to target at least the following: sucking pests such as aphids, thrips, brown plant hopper (e.g. on rice), sting bugs, white flies (e.g. on cotton and vegetables), mites; on soil pests such as corn rootworm, wireworms, white grubs, zabrus, termites (e.g. on sugar cane, soy, pasture), maggots, cabbage root fly, red legged earth mite; on lepidoptera, such as *spodoptera*, cutworms, *elasmoplpus*, *plutella* (e.g. *brassica*), stem borers, leaf miners, flea beetle, *Sternechus*; on nematicides, such as *Heterodera glycines* (e.g. on soybean), *Pratylenchus brachyurus* (e.g. on corn), *P. zeae* (e.g. oncorn), *P. penetrans* (e.g. on corn), *Meloidogyne incognita* (e.g. on vegetables), *Heterodera schachtii* (e.g. on sugar beet), *Rotylenchus reniformis* (e.g. on cotton), *Heterodera avenae* (e.g. on cereals), *Pratylenchus neglectus* (e.g. on cereals), *thornei* (e.g. on cereals).

In one embodiment the methods and uses of the invention are for controlling and/or preventing infestation of useful plants by corn rootworm, wireworms, grubs, in particular white grubs, termites, subterraneous stinkbugs, cutworms, millipedes and broca gigante that are resistant to other insecticides. Corn rootworm, wireworms, grubs and whitefly that are "resistant" to a particular insecticide refers e.g. to strains of corn rootworm, wireworms, grubs and whitefly that are less sensitive to that insecticide compared to the expected sensitivity of the same species of the respective pest. The expected sensitivity can be measured using e.g. a strain that has not previously been exposed to the insecticide.

Useful plants include soybean, corn, sugarcane, alfalfa, brassicas, oilseed rape (e.g. canola), potatoes (including sweet potatoes), cotton, rice, coffee, citrus, almonds, fruiting vegetables, cucurbits and pulses (e.g. tomatoes, pepper, chili, eggplant, cucumber, squash etc.), tea, bulb vegetables (e.g. onion, leek etc.), grapes, pome fruit (e.g. apples, pears etc.), stone fruit (e.g. pears, plums etc.), and cereals.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of a plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

Application of the compound of formula I may be before infestation or before the pest is present, or may be after the presence of the pest or at the time of infestation.

The compound of formula I may be applied directly to soil or may be applied to soil by treating plant propagation material, e.g. a seed, with the compound of formula I.

Methods of applying to the soil can be via any suitable method, which ensures that the combination penetrates the soil, for example, nursery tray application, in furrow application, soil drenching, soil injection, drip irrigation, application through sprinklers or central pivot, incorporation into soil (broad cast or in band) are such methods. Alternatively or in addition one or more materials may be applied on a suitable substrate, for example a seed which is not intended for germination, and "sowing" the treated substrate with the plant propagation material. A preferred method of applying to soil is in-furrow at sowing, e.g. as liquid spray or as granule. An extension to in-furrow application is so-called t-band application at sowing in which some of the spray or granule is additionally deposited at the soil surface.

Methods for applying or treating active ingredients on to plant propagation material, especially seeds, are known in the art, and include dressing, coating, pelleting and soaking application methods of the propagation material. Conventional treating techniques and machines can be used, such as fluidized beds, roller mills, rotostatic seed treaters, drum coaters, and spouted beds.

Even distribution of ingredients and good adherence is particularly desired for seed treatment. Treatment could vary from a thin film or dressing of the formulation, for example, a mixture of active ingredients, on a plant propagation material, such as a seed, where the original size and/or shape are recognizable to an intermediary state to a thicker film such as pelleting with many layers of different materials (such as carriers, for example, clays; different formulations, such as of other active ingredients; polymers; and colourants) where the original shape and/or size of the seed is no longer recognisable.

Application onto plant propagation material can include controlled release coatings, wherein the ingredients of the combinations are incorporated into materials that release the ingredients over time. Examples of controlled release technologies are generally known in the art and include polymer films and waxes, wherein the ingredients may be incorporated into the controlled release material or applied between layers of materials, or both.

The compounds of the invention are suitable for use on any plant, including those that have been genetically modified to be resistant to active ingredients such as herbicides, or to produce biologically active compounds that control infestation by plant pests.

The term "plants" are to be understood as also including those plants which have been rendered tolerant to herbicides or classes of herbicides (e.g. ALS-, GS-, EPSPS-, PPO- and HPPD-inhibitors) by conventional methods of breeding or by genetic engineering. An example of a plant that has been rendered tolerant to imidazolinones, e.g. imazamox, by conventional methods of breeding is Clearfield® summer rape (canola). Examples of plants that have been rendered tolerant to herbicides by genetic engineering methods include e.g. glyphosate- and glufosinate-resistant maize varieties commercially available under the trade names RoundupReady® and LibertyLink®.

Compounds of formula I may be used on transgenic plants (including cultivars) obtained by genetic engineering methods and/or by conventional methods. These are understood as meaning plants having novel properties ("traits") which have been obtained by conventional breeding, by mutagenesis or by recombinant DNA techniques. Depending on the plant species or plant cultivars, their location and growth conditions (soils, climate, vegetation period, diet), the treatment according to the invention may also result in superadditive ("synergistic") effects.

Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products.

Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds.

Examples of transgenic plants which may be mentioned are the important crop plants, such as cereals (wheat, rice), maize, soybean, potatoes, sugar beet, tomatoes, peas and other vegetable varieties, cotton, tobacco, oilseed rape and also fruit plants (with the fruits apples, pears, citrus fruits and grapes).

Compounds of formula I may be used on transgenic plants that are capable of producing one or more pesticidal proteins which confer upon the transgenic plant tolerance or resistance to harmful pests, e.g. insect pests, nematode pests and the like. Such pesticidal proteins include, without limitation, Cry proteins from *Bacillus thuringiensis* Cry1Ab, Cry1Ac, Cry1F, Cry2Ab, Cry2Ae, Cry3A, Cry3Bb, or Cry9C; engineered proteins such as modified Cry3A (U.S. Pat. No. 7,030,295) or Cry1A.105; or vegetative insecticidal proteins such as Vip1, Vip2 or Vip3. A full list of Bt Cry proteins and VIPs useful in the invention can be found on the worldwide web at *Bacillus thuringiensis* Toxin Nomenclature Database maintained by the University of Sussex (see also, Crickmore et al. (1998) *Microbiol. Mol. Biol. Rev.* 62:807-813). Other pesticidal proteins useful in the invention include proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. Further examples of such pesticidal proteins or transgenic plants capable of synthesizing such proteins are disclosed, e.g., in EP-A 374753, WO 93/007278, WO 95/34656, EP-A 427529, EP-A 451878, WO 03/18810 and WO 03/52073. The methods for producing such transgenic plants are generally known to the person skilled in the art and some of which are commercially available such as Agrisure®CB (P1) (corn producing Cry1Ab), Agrisure® RW (P2) (corn producing mCry3A), Agrisure® Viptera (P3) (corn hybrids producing Vip3Aa); Agrisure300GT (P4) (corn hybrids producing Cry1Ab and mCry3A); YieldGard® (P5) (corn hybrids producing the Cry1Ab protein), YieldGard® Plus (P6) (corn hybrids producing Cry1Ab and Cry3Bb1), Genuity® SmartStax® (P7) (corn hybrids with Cry1A.105, Cry2Ab2, Cry1F, Cry34/35, Cry3Bb); Herculex® I (P8) (corn hybrids producing Cry1Fa) and Herculex® RW (P9) (corn hybrids producing Cry34Ab1, Cry35Ab1 and the enzyme Phosphinothricin-N-Acetyltransferase [PAT]); NuCOTN® 33B (P10) (cotton cultivars producing Cry1Ac), Bollgard®I (P11) (cotton cultivars producing Cry1Ac), Bollgard®II (P12) (cotton cultivars producing Cry1Ac and Cry2Ab2) and VIPCOT® (P13) (cotton cultivars producing a Vip3Aa). Soybean Cyst Nematode resistance soybean (SCN®—Syngenta (P14)) and soybean with Aphid resistant trait (AMT® (P15)) are also of interest.

Further examples of such transgenic crops are:

1. Bt11 Maize from Syngenta Seeds SAS, Chemin de l'Hobit 27, F-31 790 St. Sauveur, France, registration number C/FR/96/05/10 (P16). Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10 (P17). Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10 (P18). Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9 (P19). MON 863 expresses a CryIIIB (b1) toxin and has resistance to certain Coleoptera insects.

5. IPC 531 Cotton from Monsanto Europe S.A. 270-272 Avenue de Tervuren, B-1150 Brussels, Belgium, registration number C/ES/96/02. (P20)

6. 1507 Maize from Pioneer Overseas Corporation, Avenue Tedesco, 7 B-1160 Brussels, Belgium, registration number C/NL/00/10. (P21) Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain Lepidoptera, include the European corn borer.

Further examples of transgenic plants, and of very high interest, are those carrying traits conferring resistance to 2.4D (e.g. Enlist®) (e.g. WO 2011066384) (, glyphosate (e.g. Roundup Ready® (P24), Roundup Ready 2 Yield® (P25)), sulfonylurea (e.g. STS®) (P26), glufosinate (e.g. Liberty Link® (P27), Ignite® (P28)), Dicamba (P29) (Monsanto), HPPD tolerance (P30) (e.g. isoxaflutole herbicide) (Bayer CropScience, Syngenta). Double or triple stacks of any of the traits described here are also of interest, including glyphosate and sulfonyl-urea tolerance ((e.g. Optimum GAT®) (P31), plants stacked with STS® and Roundup Ready® (P32) or plants stacked with STS® and Roundup Ready 2 Yield® (P33)), dicamba and glyphosate tolerance (P34) (Monsanto). Of particular interest are soybean plants carrying trains conferring resistance to 2.4D (e.g. Enlist®), glyphosate (e.g. Roundup Ready®, Roundup Ready 2 Yield®), sulfonylurea (e.g. STS®), glufosinate (e.g. Liberty Link®, Ignite®), Dicamba (Monsanto) HPPD tolerance (e.g. isoxaflutole herbicide) (Bayer CropScience, Syngenta).

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

Examples of cotton transgenic events include MON 531/757/1076 (Bollgard I®—Monsanto), MON1445 (Roundup ready Cotton®—Monsanto), MON531×MON1445 (Bollgard I+RR®—Monsanto), MON15985 (Genuity Bollgard II Cotton®—Monsanto), MON88913 (Genuity RR FLEX Cotton®—Monsanto), MON15985×MON1445 (Genuity Bollgard II+RR FLEX Cotton®—Monsanto), MON15983×MON88913 (Genuity Bollgard II+RR FLEX Cotton®—Monsanto), MON15985 (FibreMax Bollgard II Cotton®—Monsanto), LL25 (FibreMax LL Cotton®—BCS Stoneville), GHB614 (FibreMax GlyTol Cotton®—BCS Stoneville), LL25×MON15985 (FibreMax LL Bollgard II Cotton®—BCS Stoneville/Monsanto), GHB614×LL25 (FibreMax LL GlyTol Cotton®—BCS Stoneville), GHB614×LL25×MON15985 (FibreMax RR GlyTol Bollgard II Cotton®—BCS Stoneville), MON88913×MON15985 (FibreMax LL GlyTol Bollgard II Cotton®—Monsanto), MON88913 (FibreMax RR Flex Cotton®—Monsanto), GHB119+T304-40 (Twinlink®—BCS Stoneville), GHB119+T304-40×LL25×GHB614 (Twinlink LL GT®—BCS Stoneville), 3006-210-23×281-24-236 (PhytoGen Widestrike Insect Protection®—Dow), 3006-210-23×281-24-236×MON88913 (PhytoGen Widestrike Insect Protection+RR FLEX—® Dow/Monsanto), 3006-210-23×281-24-236×MON1445 ((PhytoGen Widestrike Insect Protection+RR®—Dow/Monsanto), MON1445 (PhytoGen Roundup Ready®—Monsanto), MON88913 (PhytoGen Roundup Ready FLEX®—Monsanto), COT102×COT67B (Vipcot®—Syngenta), COT102×COT67B×MON88913 (Vipcot RR FLEX®—Syngenta/Monsanto), 281-24-236 (Dow), 3006-210-23 (Dow), COT102 (Syngenta), COT67B (Syngenta), T304-40 (BCS Stoneville).

Examples of Soy transgenic events include MON87701×MON89788 (Genuity Roundup ready 2 Yield Soybeans®—Monsanto), MON89788 (Roundup Ready2Yield®, RR2Y®—Monsanto), MON87708 (Monsanto), 40-3-2 (Roundup Ready®, RR1®—Monsanto), MON87701 (Monsanto), DAS-68416 (Enlist Weed Control System®—Dow), DP356043 (Optimum GAT®—Pioneer), A5547-127 (LibertyLink Soybean®—Bayercropscience), A2704-12 (Bayercropscience), GU262 (Bayercropscience), W62 W98 (Bayercropscience), CRV127 (Cultivance®—BASF/EMBRAPA) SYHT0H2 (WO2012/082548).

Examples of Maize transgenic events include T25 (LibertyLink®, LL®—Bayerscropscience), DHT-1 (Dow), TC1507 (Herculex I®—Dow), DAS59122-7 (Herculex RW®—Dow), TC1507+DAS59122-7—Herculex Xtra®—Dow), TC1507×DAS-59122-7×NK603 (Herculex Xtra+RR®—Dow), TC1507×DAS-59122—×MON88017×MON89034 (Genuity Smartstax Corn®, Genuity Smartstax RIB Complete®—Monsanto/Dow), MON89034×NK603 (Genuity VT double PRO®—Monsanto), MON89034+MON88017 (Genuity VT Triple PRO®—Monsanto), NK603 (Roundup Ready 2®, RR2®—Monsanto), MON810 (YieldGard BT®, Yieldgard Cornborer®—Monsanto), MON810×NK603 (YieldGard cornborer RR Corn 2®—Monsanto), MON810×MON863 (YieldGard Plus®—Monsanto), MON863×MON810×NK603 (YieldGard Plus+RR Corn2®/YieldGard RR Maize®—Monsanto), MON863×NK603 (YieldGard Rotworm+RR Corn 2®—Monsanto), MON863 (YieldBard RW®—Monsanto), MON89034 (YieldGard RW®—Monsanto), MON88017 (YieldGard VT RW®—Monsanto), MON810+MON88017 (YieldGard VT Triple®—Monsanto), MON88017+MON89034 (YieldGard VT Triple Pro®—Monsanto), Bt11+MIR604+GA21 (Agrisure 3000®—Syngenta), Bt11+TC1507+MIR604+5307+GA21 (Syngenta), Bt11+

TC1507+MIR604+DAS59122+GA21 (Agrisure 3122®—Syngenta), BT11 (Agrisure CB®—Syngenta), GA21—(Agrisure GT®—Syngenta), MIR604 (Agrisure RW®—Syngenta), Bt11+MIR162 (Agrisure TL VIP®—Syngenta), BT11+MIR162+GA21 (Agrisure Viptra 3110®—Syngenta), BT11+MIR162+MIR604 (Agrisure TM 3100®—Syngenta), Event3272+BT11+MIR604+GA21 (Syngenta), BT11+MIR1692+MIR604+GA21 (Agrisure Viptera 3111®—Syngenta), BT11+MIR162+TC1507+GA21 (Agrisure Viptera 3220®—Syngenta), BT11+MIR162+TC1507+MIR604+5307+GA21 (Agrisure Viptera 3222®—Syngenta), MIR162 (Syngenta), BT11+GA21+MIR162+MIR604+5307 (Syngenta), 5307 (Syngenta).

Herbicide-resistant plants (plants bred in a conventional manner for herbicide tolerance) which may be mentioned include the varieties sold under the name Clearfield® (for example maize).

These statements also apply to plant cultivars having these genetic traits or genetic traits still to be developed, which plant cultivars will be developed and/or marketed in the future.

A compound of the invention may be used in mixtures with fertilizers (for example nitrogen-, potassium- or phosphorus-containing fertilizers). Suitable formulation types include granules of fertilizer. The mixtures preferably contain up to 25% by weight of the compound of the invention.

The invention therefore also provides a fertilizer composition comprising a fertilizer and a compound of the invention.

The compositions of this invention may contain other compounds having biological activity, for example micronutrients or compounds having fungicidal activity or which possess plant growth regulating, herbicidal, insecticidal, nematicidal or acaricidal activity.

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, e.g. a insecticide, fungicide or herbicide, or a synergist or plant growth regulator where appropriate. An additional active ingredient may provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin and gamma cyhalothrin), bifenthrin, fenpropathrin, cyfluthrin, tefluthrin, fish safe pyrethroids (for example ethofenprox), natural pyrethrin, tetramethrin, S-bioallethrin, fenfluthrin, prallethrin, acrinathrin, etofenprox or 5-benzyl-3-furylmethyl-(E)-(1R,3S)-2,2-dimethyl-3-(2-oxothiolan-3-ylidenemethyl)cyclopropane carboxylate;

b) Organophosphates, such as profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron, diafenthiuron, lufeneron, novaluron, noviflumuron or chlorfluazuron;

e) Organic tin compounds, such as cyhexatin, fenbutatin oxide or azocyclotin;

f) Pyrazoles, such as tebufenpyrad, tolfenpyrad, ethiprole, pyriprole, fipronil, and fenpyroximate;

g) Macrolides, such as avermectins or milbemycins, for example abamectin, emamectin benzoate, ivermectin, milbemycin, spinosad, azadirachtin, milbemectin, lepimectin or spinetoram;

h) Hormones or pheromones;

i) Organochlorine compounds, such as endosulfan (in particular alpha-endosulfan), benzene hexachloride, DDT, chlordane or dieldrin;

j) Amidines, such as chlordimeform or amitraz;

k) Fumigant agents, such as chloropicrin, dichloropropane, methyl bromide or metam;

l) Neonicotinoid compounds, such as imidacloprid, thiacloprid, acetamiprid, nitenpyram, dinotefuran, thiamethoxam, clothianidin, or nithiazine;

m) Diacylhydrazines, such as tebufenozide, chromafenozide or methoxyfenozide;

n) Diphenyl ethers, such as diofenolan or pyriproxifen;

o) Ureas such as Indoxacarb or metaflumizone;

p) Ketoenols, such as Spirotetramat, spirodiclofen or spiromesifen;

q) Diamides, such as flubendiamide, chlorantraniliprole (Rynaxypyr®) or cyantraniliprole;

r) Essential oils such as Bugoil®—(PlantImpact); or s) a compound selected from buprofezine, flonicamid, acequinocyl, bifenazate, cyenopyrafen, cyflumetofen, etoxazole, flometoquin, fluacrypyrim, fluensulfone, flufenerim, flupyradifuone, harpin, iodomethane, dodecadienol, pyridaben, pyridalyl, pyrimidifen, flupyradifurone, 4-[(6-Chloro-pyridin-3-ylmethyl)-(2,2-difluoro-ethyl)-amino]-5H-furan-2-one (DE 102006015467), CAS: 915972-17-7 (WO 2006129714; WO2011/147953; WO2011/147952), CAS: 26914-55-8 (WO 2007020986), chlorfenapyr, pymetrozine, sulfoxaflor and pyrifluqinazon.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxy-iminoacetamide (SSF-129), 4-bromo-2-cyano-N, N-dimethyl-6-trifluoromethylbenzimidazole-1-sulfonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy)propionamide (AC382042), N-(2-methoxy-5-pyridyl)-cyclopropane carboxamide, acibenzolar (CGA245704) (e.g. acibenzolar-S-methyl), alanycarb, aldimorph, anilazine, azaconazole, azoxystrobin, benalaxyl, benomyl, benthiavalicarb, biloxazol, bitertanol, bixafen, blasticidin S, boscalid, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulfate, copper tallate and Bordeaux mixture, cyclufenamid, cymoxanil, cyproconazole, cyprodinil, debacarb, di-2-pyridyl disulfide 1,1'-dioxide, dichlofluanid, diclomezine, dicloran, diethofencarb, difenoconazole, difenzoquat, diflumetorim, O,O-di-iso-propyl-S-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl-(Z)-N-benzyl-N-([methyl(methyl-thioethylideneamino-oxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluopyram, fluoxastrobin, fluoroimide, fluquinconazole, flusilazole, flutolanil, flutriafol, fluxapyroxad, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, isopyrazam, kasugamycin, kresoxim-methyl, LY186054, LY211795, LY248908, mancozeb, mandipropamid, maneb, mefenoxam, metalaxyl, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, penflufen, penthiopyrad, phenazin oxide, phosetyl-A1, phosphorus acids, phthalide, picoxystrobin (ZA1963), polyoxinD, polyram, probenazole, prochloraz, procymidone, propamocarb, propiconazole, propineb, propionic acid, prothioconazole, pyrazophos, pyrifenox, pyrimethanil, pyraclostrobin, pyroquilon, pyroxyfur, pyrrolnitrin, quaternary ammonium compounds, quinomethionate, quinoxyfen, quintozene, sedaxane, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram, N-[9-(dichloromethylene)-1,2,3,4-tetrahydro-1,4-methanonaphthalen-5-yl]-3-(difluoromethyl)-1-methyl-1H-pyrazole-4-carboxamide[1072957-71-1], 1-methyl-3-difluoromethyl-1H-pyrazole-4-carboxylic acid (2-dichloromethylene-3-ethyl-1-methyl-indan-4-yl)-amide, and 1-methyl-3-difluoromethyl-4H-pyrazole-4-carboxylic acid [2-(2,4-dichloro-phenyl)-2-methoxy-1-methyl-ethyl]-amide.

In addition, biological agents may be included in the composition of the invention e.g. *Baciullus* species such as *Bacillus firmus, Bacillus cereus, Bacillus subtilis*, and *Pasteuria* species such as *Pasteuria penetrans* and *Pasteuria nishizawae*. A suitable *Bacillus firmus* strain is strain CNCM I-1582 which is commercially available as BioNem™. A suitable *Bacillus cereus* strain is strain CNCM I-1562. Of both *Bacillus* strains more details can be found in U.S. Pat. No. 6,406,690. Other biological organisms that may be included in the compositions of the invention are bacteria such as *Streptomyces* spp. such as *S. avermitilis*, and fungi such as *Pochonia* spp. such as *P. chlamydosporia*. Also of interest are *Metarhizium* spp. such as *M. anisopliae; Pochonia* spp. such as *P. chlamydosporia*.

Preferred mixing partners are abamectin and/or pymetrozine.

The compounds of the invention may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

For soil applications using compounds of formula I on sugar cane, including application on sugar cane propogation material such as buds, the following mixing partners are of particular interest: insecticides selected from neonicotinoids, in particular thiamethoxam, imidacloprid and clothianidin, sulfoxaflor, abamectin, carbofuran, tefluthrin, fipronil, ethiprole, spinosad, lamda-cyhalothrin, bisamides, in particular chlorantraniliprole, cyantraniliprole, flubendiamide; optionally with fungicides selected from azoxystrobin, cyproconazole, thiabendazole, fluazinam, fludioxonil, mefenoxam, Sedaxane. Particular combinations of interest for sugar cane, particularly on sugar cane propogation material such as buds, include a compound of formula I with thiamethoxam and abamectin, a compound of formula I with thiamethoxam and cyantraniliprole, a compound of formula I with thiamethoxam and chlorantraniliprole. Further combinations of particular interest for sugar cane include a compound selected from Tables A to F+thiamethoxam+abamectin+mefenoxam+fludioxonil+azoxystrobin+thiabendazole; a compound selected from Tables A to F+abamectin+mefenoxam+fludioxonil+azoxystrobin+thiabendazole, a compound selected from Tables A to F+thiamethoxam+mefenoxam+fludioxonil+azoxystrobin+ thiabendazole, a compound selected from Tables A to F+thiamethoxam+abamectin+mefenoxam+fludioxonil+ azoxystrobin+thiabendazole, a compound selected from Tables A to F+thiamethoxam+abamectin+fludioxonil+azoxystrobin+thiabendazole, a compound selected from Tables A to F+thiamethoxam+abamectin+mefenoxam+azoxystrobin+ thiabendazole, a compound selected from Tables A to F+thiamethoxam+abamectin+mefenoxam+fludioxonil+thiabendazole, a compound selected from Tables A to F+thiamethoxam+abamectin+mefenoxam+fludioxonil+azoxystrobin. Example of ratios are below.

Unless otherwise stated the weight ratio of the compound of I with an additional active ingredient may generally be between 1000:1 and 1:1000. In other embodiments that weight ratio of A to B may be between 500:1 to 1:500, for example between 100:1 to 1:100, for example between 1:50 to 50:1, for example 1:20 to 20:1, for example 1:10 to 10:1, for example 1:5 to 5:1, for example 1:1, 1:2, 1:3, 1:4, 1:5, 2:1, 3:1, 4:1, or 5:1.

In general, mixtures thiamethoxam, imidacloprid and clothianidin are of particular interest, as well as with pymetrozine and abamectin.

Compositions of the invention include those prepared by premixing prior to application, e.g. as a readymix or tank-mix, or by simultaneous application or sequential application to the plant.

In order to apply a compounds of the invention as an insecticide, acaricide, nematicide or molluscicide to a pest, a locus of pest, or to a plant susceptible to attack by a pest, compounds of the invention is usually formulated into a composition which includes, in addition to the compound of the invention, a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of the invention. The composition is generally used for the control of pests such that a compound of the invention is applied at a rate of from 0.1 g to 10 kg per hectare, preferably from 1 g to 6 kg per hectare, more preferably from 1 g to 1 kg per hectare.

Compositions comprising a compound of the invention can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of the invention.

Dustable powders (DP) may be prepared by mixing a compound of the invention with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of the invention with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of the invention with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of the invention and one or more powdered solid diluents or carriers, or from pre-formed blank granules by absorbing a compound of the invention (or a solution thereof, in a suitable agent) in a porous granular material (such as pumice, attapulgite clays, fuller's earth, kieselguhr, diatomaceous earths or ground corn cobs) or by adsorbing a compound of the invention (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of the invention in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of the invention in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of the invention either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of the invention is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of the invention. SCs may be prepared by ball or bead milling the solid compound of the invention in a suitable medium, optionally with one or more dispersing agents, to produce a fine particle suspension of the compound. One or more wetting agents may be included in the composition and a suspending agent may be included to reduce the rate at which the particles settle. Alternatively, a compound of the invention may be dry milled and added to water, containing agents hereinbefore described, to produce the desired end product.

Aerosol formulations comprise a compound of the invention and a suitable propellant (for example n-butane). A compound of the invention may also be dissolved or dispersed in a suitable medium (for example water or a water miscible liquid, such as n-propanol) to provide compositions for use in non-pressurized, hand-actuated spray pumps.

A compound of the invention may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of the invention and, optionally, a carrier or diluent therefor. The polymeric shell may be produced by either an interfacial polycondensation reaction or by a coacervation procedure. The compositions may provide for controlled release of the compound of the invention and they may be used for seed treatment. A compound of the invention may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of the invention). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of the invention).

A compound of the invention may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of the invention (for example 0.0001 to 10%, by weight) depending upon the purpose for which they are to be used.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules. A typical a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation. A typical pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

The rates of application of a plant propagation material treatment varies, for example, according to type of use, type of crop, the specific compound(s) and/or agent(s) used, and type of plant propagation material. The suitable rate is an effective amount to provide the desired action (such as disease or pest control) and can be determined by trials and routine experimentation known to one of ordinary skill in the art.

Generally for soil treatments, application rates can vary from 0.05 to 3 kg per hectare (g/ha) of ingredients. Generally for seed treatments, application rates can vary from 0.5 to 1000 g/100 kg of seeds of ingredients.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of formula I together with a compound of component B, and optionally other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

FORMULATION EXAMPLES

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The combination is thoroughly mixed with the adjuvants and the mixture is thoroughly ground in a suitable mill, affording powders that can be used directly for seed treatment.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

Suspension Concentrate

| | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, seeds can be treated and protected against infestation by spraying, pouring or immersion.

Flowable Concentrate for Seed Treatment

| | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, seeds can be treated and protected against infestation by spraying, pouring or immersion.

The invention further pertains to a product for use in agriculture or horticulture comprising a capsule wherein at least a seed treated with the inventive compound is located. In another embodiment, the product comprises a capsule wherein at least a treated or untreated seed and the inventive compound are located.

Slow Release Capsule Suspension 28 parts of the inventive compound are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredient. The medium capsule diameter is 8-15 microns. The resulting formulation is applied to seeds as an aqueous suspension in a suitable apparatus.

The invention will now be illustrated by the following non-limiting Examples. All citations are incorporated by reference.

BIOLOGICAL EXAMPLES

TABLE A

TABLE A provides compounds of formula (Ia) where in $X^1$ and $R^1$ have the definition shown below.

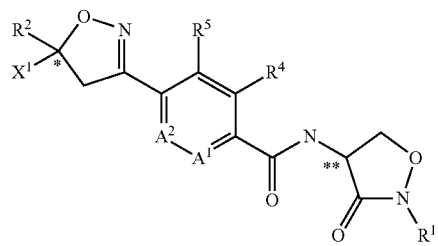

(Ia)

| | X1 | R1 | R2 | A1 | A2 | R4 | R5 | Stereo-chemistry at * | Stereo-chemistry at ** |
|---|---|---|---|---|---|---|---|---|---|
| A01 | 3,4,5-trichlorophenyl | 2,2,2-trifluoroethyl | CF3 | CH | CH | CH3 | H | S | R/S |
| A02 | 3,5-dichlorophenyl | methyl | CF3 | CH | CH | CH3 | H | S | R/S |
| A03 | 3,5-dichlorophenyl | 2,2,2-trifluoroethyl | CF3 | CH | CH | CH3 | H | S | S |
| A04 | 3,5-dichlorophenyl | ethyl | CF3 | CH | CH | CH3 | H | S | S |
| A05 | 3,5-dichloro-4-fluorophenyl | Ethyl | CF3 | CH | CH | CH3 | H | S | R/S |
| A06 | 3,5-dichlorophenyl | 2,2-difluoroethyl | CF3 | CH | CH | CH3 | H | S | R/S |
| A08 | 3,5-dichlorophenyl | 2,2,2-trifluoroethyl | CF3 | CH | CH | CH3 | H | S | R/S |
| A09 | 3,5-dichlorophenyl | ethyl | CF3 | CH | CH | CH3 | H | S | R/S |
| A10 | 3-bromo-5-chlorophenyl | 2,2,2-trifluoroethyl | CF3 | CH | CH | CH3 | H | R/S | R |
| A11 | 3-chloro-5-bromophenyl | ethyl | CF3 | CH | CH | CH3 | H | S | R |
| A12 | 3-chloro-5-trifluoromethyl-phenyl | ethyl | CF3 | CH | CH | CH3 | H | S | R |
| A14 | 3,5-dichlorophenyl | 2,2-difluoroethyl | CF3 | CH | CH | CH3 | H | S | R |
| A15 | 3,5-trifluoromethyl-4-chlorophenyl | ethyl | CF3 | CH | CH | CH3 | H | R/S | R |
| A16 | 3,5-dichlorophenyl | 2,2,2-trifluoroethyl | CF3 | CH | CH | CH3 | H | S | R |
| A17 | 3,5-dichlorophenyl | ethyl | CF3 | CH | CH | CH3 | H | S | R |
| A18 | 3,5-dichloro-4-fluorophenyl | ethyl | CF3 | CH | CH | CH3 | H | S | R |
| A19 | 3,4,5-trichlorophenyl | ethyl | CF3 | CH | CH | CH3 | H | S | R |
| A20 | 3,5-dichloro-4-fluorophenyl | 2,2,2-trifluoroethyl | CF3 | CH | CH | CH3 | H | S | R |
| A21 | 3,4,5-trichlorophenyl | 2,2,2-trifluoroethyl | CF3 | CH | CH | CH3 | H | S | R |
| A22 | 3-chloro-5-fluorophenyl | ethyl | CF3 | CH | CH | CH3 | H | R/S | R |
| A23 | 3,4,5-trichlorophenyl | ethyl | CF3 | CH | CH | CH3 | H | R/S | R |
| A24 | 3,4,5-trichlorophenyl | ethyl | CF3 | CH | CH | Cl | H | S | R |
| A25 | 3,5-dichlorophenyl | ethyl | CF3 | CH | CH | Br | H | S | R |
| A26 | 3,4,5-trichlorophenyl | ethyl | CF3 | CH | CH | Br | H | S | R |
| A27 | 3,5-dichlorophenyl | ethyl | CF3 | CH | CH | CF3 | H | S | R |
| A28 | 3,4,5-trichlorophenyl | ethyl | CF3 | CH | CH | CF3 | H | S | R |
| A29 | 3-trifluoromethylphenyl | ethyl | CF3 | CH | CH | CH3 | H | S | R |

TABLE A-continued

TABLE A provides compounds of formula (Ia) where in $X^1$ and $R^1$ have the definition shown below.

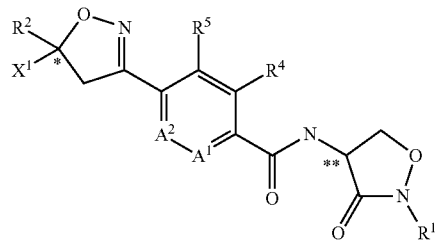

(Ia)

| | X1 | R1 | R2 | A1 | A2 | R4 | R5 | Stereochemistry at * | Stereochemistry at ** |
|---|---|---|---|---|---|---|---|---|---|
| A30 | 3-chloro,5-trifluoromethylphenyl | ethyl | CF3 | CH | CH | CH=CH—CH=CH | | S | R |
| A31 | 3,5-dichloro-4-fluorophenyl | ethyl | CF3 | CH | CH | Cl | H | S | R |
| A32 | 3,5-dichlorophenyl | 2,2,2-trifluorobutyl | CF3 | CH | CH | CH3 | H | R/S | R |
| A33 | 3,5-dichlorophenyl | 2,2,2-trifluoropropyl | CF3 | CH | CH | CH3 | H | R/S | R |
| A34 | 3-chloro-5-trifluoromethylphenyl | 2,2,2-trifluoroethyl | CF3 | CH | CH | CH3 | H | R/S | R |
| A35 | 3,5-dichlorophenyl | 2,2,2-trifluoroethyl | CF3 | CH | CH | CH=CH—CH=CH | | R/S | R |
| A36 | 3,5-dichlorophenyl | 2,2,2-trifluoroethyl | CF3 | CH | CH | Br | H | R/S | R |
| A37 | 3-bromo-5-chlorophenyl | ethyl | CF3 | CH | CH | CH3 | H | R/S | R |
| A38 | 3-chloro-5-trifluoromethylphenyl | ethyl | CF3 | CH | CH | CH3 | H | R/S | R |
| A39 | 3,5-dichlorophenyl | ethyl | CF3 | CH | CH | CH=CH—CH=CH | | R/S | R |
| A40 | 3,5-dichlorophenyl | ethyl | CF3 | CH | CH | Br | H | R/S | R |
| A41 | 3,5-dichlorophenyl | ethyl | CF3 | CH | CH | CH3 | H | R/S | R |
| A42 | 3,5-dichlorophenyl | Cyclobutyl | CF3 | CH | CH | CH3 | H | R/S | R |
| A43 | 3,5-dichlorophenyl | butyl | CF3 | CH | CH | CH3 | H | R/S | R |
| A44 | 3,5-dichlorophenyl | 2,2,2-trifluoroethyl | CF3 | CH | CH | CH3 | H | R/S | R |
| A45 | 3,5-dichlorophenyl | methyl | CF3 | CH | CH | CH3 | H | R/S | R |
| A46 | 3,5-dichlorophenyl | 2,2-difluoroethyl | CF3 | CH | CH | CH3 | H | S | S |
| A47 | 3,5-dichlorophenyl | 2,2,2-trifluoroethyl | CF3 | CH | CH | CH3 | H | R/S | R/S |
| A48 | 3,5-dichlorophenyl | ethyl | CF3 | CH | CH | CH3 | H | R/S | R/S |
| A49 | 3-chloro-5-bromophenyl | 2,2,2-trifluoroethyl | CF3 | CH | CH | CH3 | H | R | R |
| A50 | 3-chloro-5-bromophenyl | 2,2,2-trifluoroethyl | CF3 | CH | CH | CH3 | H | S | R |
| A51 | 3-chloro-5-bromophenyl | ethyl | CF3 | CH | CH | CH3 | H | R | R |
| A52 | 3-chloro-5-trifluoromethylphenyl | ethyl | CF3 | CH | CH | CH3 | H | R | R |
| A53 | 3,5-dichloro-4-fluorophenyl | 2,2,2-trifluoroethyl | CF3 | CH | CH | CH3 | H | R | R |
| A54 | 3,4,5-trichlorophenyl | 2,2,2-trifluoroethyl | CF3 | CH | CH | CH3 | H | R | R |
| A55 | 3,5-dichloro-4-fluorophenyl | ethyl | CF3 | CH | CH | CH3 | H | R/S | R |
| A56 | 3,5-dichloro-4-bromophenyl | ethyl | CF3 | CH | CH | CH3 | H | R/S | R |
| A57 | 3,5-dichloro-phenyl | methyl | CF3 | CH | CH | CH3 | H | R/S | S |
| A58 | 3,5-dichloro-phenyl | ethyl | CF3 | CH | CH | CH3 | H | R/S | S |

TABLE A-continued

TABLE A provides compounds of formula (Ia) where in $X^1$ and $R^1$ have the definition shown below.

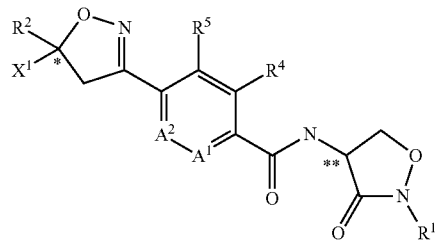

(Ia)

| | X1 | R1 | R2 | A1 | A2 | R4 | R5 | Stereochemistry at * | Stereochemistry at ** |
|---|---|---|---|---|---|---|---|---|---|
| A59 | 3,5-dichlorophenyl | 2,2,2-trifluoroethyl | CF2Cl | CH | CH | CH3 | H | R/S | R |
| A60 | 3,5-dichlorophenyl | ethyl | CF2Cl | CH | CH | CH3 | H | R/S | R |
| A61 | 3,5-dichlorophenyl | 2,2,2-trifluoroethyl | CF3 | N | CH | H | H | R/S | R |
| A62 | 3,5-dichlorophenyl | ethyl | CF3 | N | CH | H | H | R/S | R |
| A63 | 3,5-dichlorophenyl | 2,2,2-trifluoroethyl | CF3 | CH | N | CH3 | H | R/S | R |
| A64 | 3,5-dichlorophenyl | ethyl | CF3 | CH | N | CH3 | H | R/S | R |

TABLE B

TABLE B provides compounds of formula (Ib) wherein $X^1$ and $R^1$ have the definitions shown below.

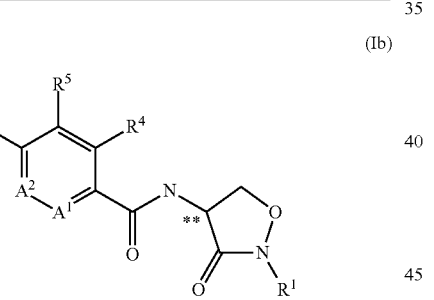

(Ib)

| | X1 | R1 | R2 | A1 | A2 | R4 | R5 | Stereochemistry at * | Stereochemistry at ** |
|---|---|---|---|---|---|---|---|---|---|
| B1 | 3,5-dichlorophenyl | ethyl | CF3 | CH | CH | CH3 | H | R/S | R |
| B2 | 3,5-dichlorophenyl | 2,2,2-trifluoroethyl | CF3 | CH | CH | CH3 | H | R/S | R |

TABLE C

TABLE C provides compounds of formula (Ic) wherein $X^1$ and $R^1$ have the definitions shown below.

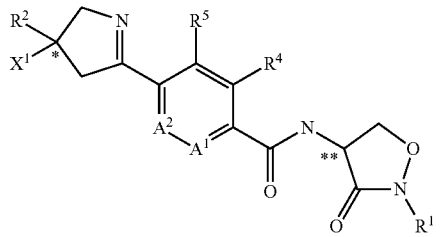

(Ic)

| | X1 | R1 | R2 | A1 | A2 | R4 | R5 | Stereochemistry at * | Stereochemistry at ** |
|---|---|---|---|---|---|---|---|---|---|
| C1 | 3,5-dichlorophenyl | 2,2,2-trifluoroethyl | CF3 | CH | CH | CH3 | H | R | R |
| C2 | 3,5-dichlorophenyl | ethyl | CF3 | CH | CH | CH3 | H | R | R |
| C3 | 3,4,5-trichlorophenyl | ethyl | CF3 | CH | CH | CH3 | H | R/S | R |
| C4 | 3,5-dichlorophenyl | 2,2,2-trifluorobutyl | CF3 | CH | CH | CH3 | H | R/S | R |
| C5 | 3,5-dichlorophenyl | 2,2,2-trifluoropropyl | CF3 | CH | CH | CH3 | H | R/S | R |

TABLE C-continued

TABLE C provides compounds of formula (Ic) wherein $X^1$ and $R^1$ have the definitions shown below.

(Ic)

| | X1 | R1 | R2 | A1 | A2 | R4 | R5 | Stereochemistry at * | Stereochemistry at ** |
|---|---|---|---|---|---|---|---|---|---|
| C6 | 3,4,5-tri-chloro-phenyl | 2,2,2-tri-fluoro-ethyl | CF3 | CH | CH | CH3 | H | R/S | R |
| C7 | 3,5-di-chloro-phenyl | ethyl | CF3 | CH | CH | CH3 | H | R/S | R |

TABLE D

TABLE D provides compounds of formula (Id) wherein $X^1$ and $R^1$ have the definitions shown below.

(Id)

| | X1 | R1 | R2 | A1 | A2 | R4 | R5 | Stereochemistry at * | Stereochemistry at ** |
|---|---|---|---|---|---|---|---|---|---|
| D1 | 3,5-di-chloro-phenyl | 2,2,2-tri-fluoro-ethyl | CF3 | CH | CH | CH3 | H | R/S | R |
| D2 | 3,5-di-chloro-phenyl | ethyl | CF3 | CH | CH | CH3 | H | R/S | R |
| D3 | 3,5-di-chloro-phenyl | 2,2,2-tri-fluoro-ethyl | CF3 | CH | N | CH3 | H | R/S | R |

R/S indicates a racemic mixture.

*Agriotes* sp. (Wireworms)

Plastic beakers are prepared with 100 ml drench soil. Afterwards 12.5 ml compound solution is mixed in each plastic beaker and three maize seedlings are added. At the same day five wireworms are placed into each plastic beaker and these are covered up with a lid. Fourteen days after treatment the number of dead and moribund wireworms are evaluated. Wireworms are assessed as moribund if they were not able to bury into the soil in one hour after having been put onto the soil surface.

| | Application rate/ppm | % Moribund & dead |
|---|---|---|
| A17 | 12.5 | 100 |
| | 3 | 100 |
| | 0.8 | 100 |
| A9 | 12.5 | 100 |
| | 3 | 75 |
| | 0.8 | 50 |
| A16 | 12.5 | 100 |
| | 3 | 100 |
| | 0.8 | 100 |

*Diabrotica Balteata* (Corn Rootworm)

Treated corn seeds are sown in a 350 ml pot filled with soil. Two weeks after sowing corn seedlings are infested with L3 larvae of *Diabrotica balteata*. After an incubation period of 6 days survived larvae are counted.

| Compound used to treat the seeds | Application rate: mg/seed | % Larval mortality |
|---|---|---|
| A23 | 1 | 100 |
| A17 | 1 | 83 |
| A14 | 1 | 100 |
| A19 | 1 | 100 |
| A21 | 1 | 100 |
| A11 | 1 | 100 |
| C2 | 1 | 50 |
| D1 | 0.3 | 83 |
| A18 | 0.3 | 96 |
| A8 | 0.3 | 79 |
| A1 | 0.3 | 87 |
| A5 | 0.3 | 96 |
| A15 | 0.3 | 100 |
| A22 | 1 | 92 |
| A20 | 1 | 100 |
| A12 | 0.3 | 88 |
| C3 | 1 | 100 |
| A16 | 1 | 100 |
| A6 | 0.3 | 87 |
| A2 | 0.3 | 96 |
| C1 | 1 | 100 |

*Diabrotica balteata* (Corn Rootworm)

A 24-well microtiter plate (MTP) with artificial diet was treated with test solutions at an application rate of 200 ppm by pipetting. After drying, the MTPs were infested with L2 larvae (6-10 per well). After an incubation period of 5 days, samples were checked for larval mortality.

The following compounds gave 100% mortality at 200 ppm: A1, A2, A3, A4, A5, A6, A8, A9, A10, A11, A12, A14, A15, A16, A17, A18, A19, A20, A21, A22, A23, A24, A25, A26, A27, A28, A29, A30, A31, A32, A33, A34, A35, A36, A37, A38, A39, A40, A41, A42, A43, A44, A45, A46, A47, A48, A49, A50, A51, A52, A53, A54, A55, A56, A57, A58, A59, A60, A61, A62, A63, A64, B1, B2, C1, C2, C3, C4, C5, C6, C7, C8, D1, D2, D3

*Agriotes* sp. (Wireworms)

Treated corn seeds are sown in a 350 ml pot filled with soil. One week after sowing corn seedlings are infested with wireworms. After an incubation period of 14 days healthy and affected larvae (intoxicated, moribund, dead) are counted.

| Compound used to treat the seeds | Application rate: mg/seed | % Mortality and moribund/intoxicated |
|---|---|---|
| A17 | 1 | 80 |
| A9 | 1 | 25 |
| A16 | 1 | 100 |
| A8 | 1 | 100 |

Termites

Washed sand is treated with the experimental compound in a volatile solvent, so as to deliver the desired concentration w/w in the solvent free sand. Once the solvent has evaporated, the sand is thoroughly mixed and made up with deionised water to 3% w/w moisture content. The treated sand is packed into a glass tube (internal diameter of 13.5 mm, length 120 mm) so that a 5 cm column of treated sand is formed in the tube, leaving ca. 1 cm free from one open end. A small section of filter paper is placed on the soil surface nearest the tube end, and sealed with a rubber bung or with aluminium foil. A ca. 2 cm bung of 7% agar is cut and pushed into the open end of the tube until it is in contact with the treated sand. Another section of filter paper is placed on the agar bung and ca. 40 worker termites, with not more than one soldier, are placed on the filter paper. The open end of the tube is then sealed with a rubber bung or aluminium foil. The so prepared tubes are held under similar conditions to their culture colony. The mortality of the termites, any unusual behaviour or symptomology, and the distance they have tunneled into the treated soil, is recorded daily for up to 21 days.

Diabrotica Balteata (Corn Rootworm):

Plastic boxes (17×27×22 cm) are filled with 8 L of drench soil and 6 maize seeds are sown into a furrow. 10 ml of spray solution are applied with a hand sprayer into the furrow on the planted seeds and the furrow is closed afterwards. Two weeks after sowing each box is infested with 15 Diabrotica balteata L2 larvae. 6 days after infestation the plant damage is assessed. Plants are considered as either damaged or healthy. Dead plants, plants with hollow stems or entry holes are considered as damaged. The test is carried out with five replicates (boxes) per treatment. For in-furrow application the control is replicated five times with the application of water.

For the assessment as seed treatment 6 treated seeds are planted 0.5 cm deep into the soil. Exactly the same setup is used as with the in furrow treatment described above except that no spray solution is applied. For seed treatment the control is replicated five times without seed coating.

As six seeds are used per replicate, the total amount of active ingredient applied in furrow is six times the rate per seed in the seed treatment test. In that way the total amount of active ingredient used in both test system is adjusted to be directly comparable.

The results show that the potency is significantly higher when the active ingredient is applied in-furrow compared to as a seed treatment.

| Compound | Application rate/mg AI per seed | Reduction in plant damage compared to control (in-furrow application)/% | Reduction in plant damage compared to control (seed treatment)/% |
|---|---|---|---|
| Compound 1 | 0.5 | 95 | 50 |
|  | 0.1 | 67 | 25 |
| Compound 2 | 0.5 | 91 | 75 |
|  | 0.1 | 95 | 35 |

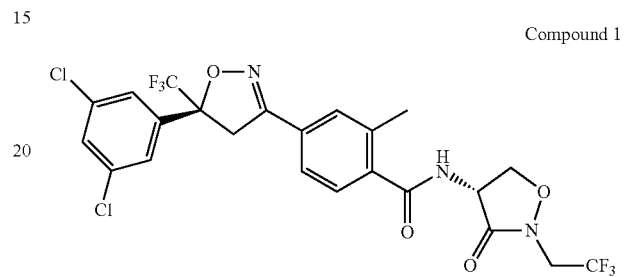

Compound 1

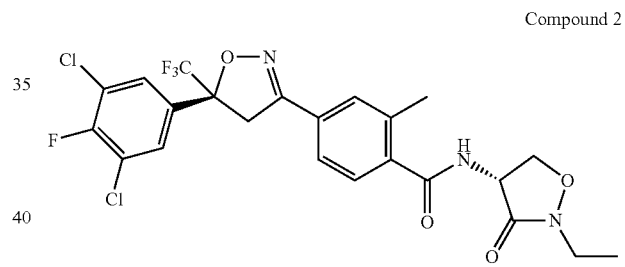

Compound 2

COMPARATIVE EXAMPLES

Agriotes sp. (Wireworms)

Plastic beakers are prepared with 100 ml drench soil. Afterwards 12.5 ml compound solution is mixed in each plastic beaker and three maize seedlings are added. At the same day five wireworms are placed into each plastic beaker and these are covered up with a lid. Fourteen days after treatment the number of dead and moribund wireworms are evaluated. Wireworms are assessed as moribund if they were not able to bury into the soil in one hour after having been put onto the soil surface.

The results show that the compounds of the invention are significantly more active against wireworms than structurally similar compounds.

Comparative Table 1

Compound of the invention

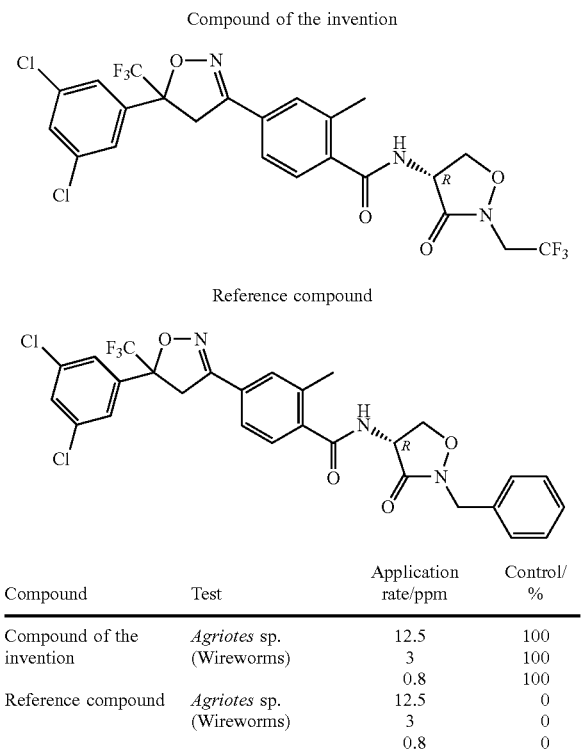

Reference compound

| Compound | Test | Application rate/ppm | Control/% |
|---|---|---|---|
| Compound of the invention | *Agriotes* sp. (Wireworms) | 12.5 | 100 |
| | | 3 | 100 |
| | | 0.8 | 100 |
| Reference compound | *Agriotes* sp. (Wireworms) | 12.5 | 0 |
| | | 3 | 0 |
| | | 0.8 | 0 |

*Diabrotica balteata* (Corn Rootworm)

A 24-well microtiter plate (MTP) with artificial diet was treated with test solutions at an application rate of 200 ppm (concentration in well 18 ppm) by pipetting. After drying, the MTPs were infested with L2 larvae (6-10 per well). After an incubation period of 5 days, samples were checked for larval mortality.

The results show that the compounds of the invention are significantly more active against *Diabrotica* balteata than structurally similar compounds.

Comparative Table 2

Compound of the invention

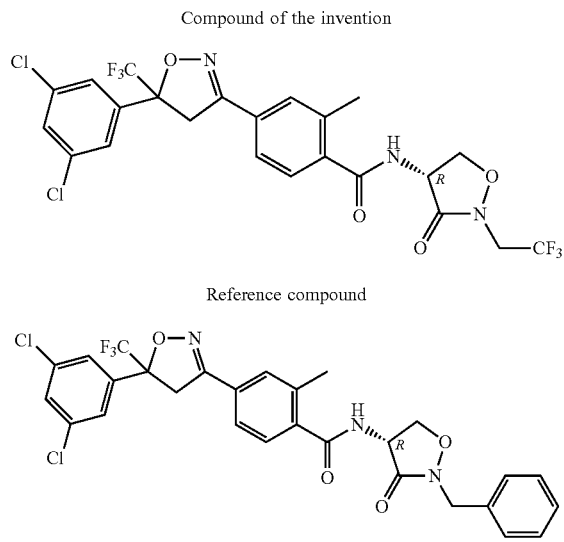

Reference compound

| Compound | Test | Application rate/ppm | Control/% |
|---|---|---|---|
| Compound of the invention | *Diabrotica balteata* (Corn rootworm) | 50 | 100 |
| | | 12.5 | 100 |
| Reference compound | *Diabrotica balteata* (Corn rootworm) | 50 | 80 |
| | | 12.5 | 0 |

The compound of the invention and reference compound are compounds B5 and B4 respectively from WO 2011/067272.

The invention claimed is:

1. A method of controlling and/or preventing soil-dwelling pests in useful plants comprising applying to the locus of the useful plant or treating plant propagation material thereof with a compound of formula I

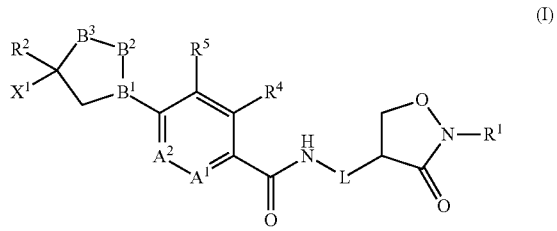

(I)

wherein
—B$^1$—B$^2$—B$^3$— is —C═N—O—, —C═N—CH$_2$—, —C═CH$_2$—O— or —N—CH$_2$—CH$_2$—;
L is a direct bond or methylene;
A$^1$ and A$^2$ are C—H, or one of A$^1$ and A$^2$ is C—H and the other is N;
X$^1$ is group X

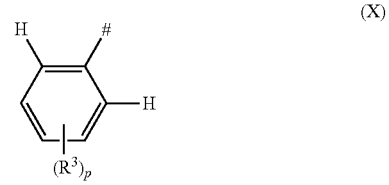

(X)

R$^1$ is C$_1$-C$_4$alkyl, C$_1$-C$_4$haloalkyl or C$_3$-C$_6$cycloalkyl;
R$^2$ is chlorodifluoromethyl or trifluoromethyl;
each R$^3$ is independently bromo, chloro, fluoro or trifluoromethyl;
R$^4$ is hydrogen, halogen, methyl, halomethyl or cyano;
R$^5$ is hydrogen;
or R$^4$ and R$^5$ together form a bridging 1,3-butadiene group;
p is 2 or 3,
and where the soil-dwelling pest includes at least one pest chosen from a wireworm; a grub; a white grub; a termite; a subterraneous stinkbug; a cutworm; a millipede; and a broca gigante.

2. A method according to claim 1, wherein the compound of formula I is applied directly to soil.

3. A method according to claim 1 wherein the compound of formula I is applied to soil by treatment of a seed with a compound of formula I.

4. A method comprising applying a compound of formula I as defined in claim 1 to a field of corn plants, before, during or after planting, and wherein the application of the compound of formula I comprises applying the compound of formula I directly to soil.

5. A method according to claim 3, wherein the compound of formula I is applied in-furrow.

6. A method according to claim 1, wherein $A^1$ and $A^2$ are C—H, $R^2$ is trifluoromethyl, and $R^5$ is hydrogen, wherein the soil-dwelling pests are optionally wireworms.

7. A method according to claim 1, wherein $A^1$ and $A^2$ are C—H, $R^2$ is trifluoromethyl, $R^4$ is methyl, $R^5$ is hydrogen, each $R^3$ is chlorine, p is 2, wherein the soil-dwelling pests are optionally wireworms.

8. A method according to claim 1, wherein $R^1$ is methyl, ethyl, propyl, butyl, cyclopropyl, cyclobutyl, trifluoroethyl, difluoroethyl, wherein the soil-dwelling pests are optionally wireworms.

9. A method according to claim 1, wherein $R^1$ is ethyl or trifluoroethyl, wherein the soil-dwelling pests are optionally wireworms.

10. A method according to claim 1, wherein $X^1$ is 3,5-dichloro-phenyl, 3,5-dichloro-4-fluorophenyl-, 3,4,5-trichlorophenyl-, or 3,5-bis(trifluoromethyl)phenyl, wherein the soil-dwelling pests are optionally wireworms.

11. A method according to claim 1, wherein —$B^1$—$B^2$—$B^3$— is —C=N—O—, wherein the soil-dwelling pests are optionally wireworms.

12. A method according to claim 1, wherein the compound of formula I is a mixture of compounds I* and I**

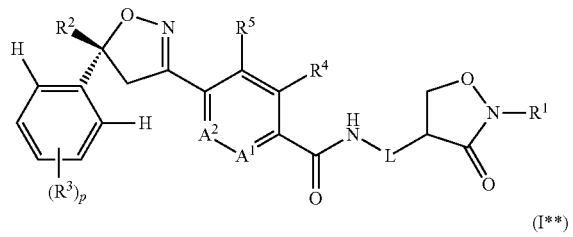

(I*)

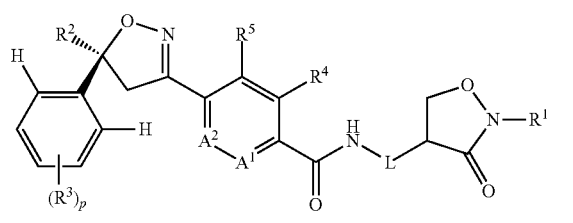

(I**)

wherein the molar proportion of compound I** compared to the total amount of both enantiomers is greater than 50%, wherein the soil-dwelling pests are optionally wireworms.

13. A method according to claim 1, wherein the compound of formula I is a mixture of compounds I' and I"

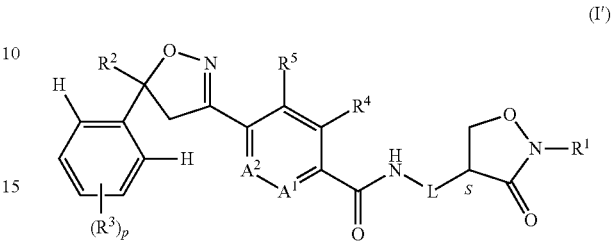

(I')

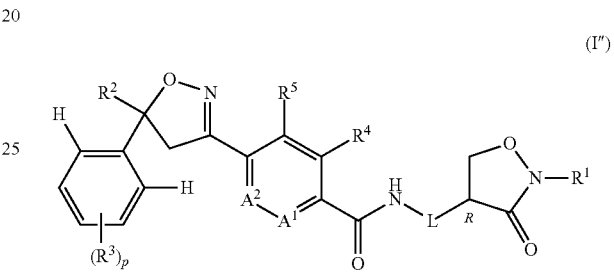

(I")

(S=S stereochemistry, R=R stereochemistry)

wherein the molar proportion of compound I" compared to the total amount of both enantiomers is greater than 50%, preferably wherein the soil-dwelling pests are wireworms.

14. A method for obtaining regulatory approval for the use of one or more of a compound of formula I as defined in claim 1 to control a pest selected from wireworms, grubs, in particular white grubs, termites, subterraneous stinkbugs, cutworms, millipedes and broca gigante, comprising at least one step of referring to, submitting or relying on biological data showing that said active ingredient reduces insect pressure.

* * * * *